United States Patent [19]

Robins et al.

[11] Patent Number: 4,880,784
[45] Date of Patent: Nov. 14, 1989

[54] ANTIVIRAL METHODS UTILIZING RIBOFURANOSYLTHIAZOLO[4,5-D]PYRIMDINE DERIVATIVES

[75] Inventors: Roland K. Robins, Irvine; Howard B. Cottam, Fallbrook, both of Calif.

[73] Assignee: Brigham Young University, Provo, Utah

[21] Appl. No.: 136,020

[22] Filed: Dec. 21, 1987

[51] Int. Cl.$^4$ .................... A61K 31/665; A61K 31/67
[52] U.S. Cl. .......................... 514/48; 514/45; 514/46; 514/47; 536/27
[58] Field of Search ............................ 536/24; 514/43; 544/255

[56] References Cited

U.S. PATENT DOCUMENTS

| | | | |
|---|---|---|---|
| 3,277,093 | 10/1966 | Schroeder | 544/255 |
| 3,660,405 | 5/1972 | Berger et al. | 544/255 |
| 4,309,419 | 1/1982 | Wolberg et al. | |
| 4,539,205 | 9/1985 | Goodman | 514/45 |
| 4,643,992 | 2/1987 | Goodman | 514/45 |
| 4,746,651 | 5/1988 | Goodman | 514/45 |

FOREIGN PATENT DOCUMENTS

| | | | |
|---|---|---|---|
| 0713652 | 9/1954 | United Kingdom | 544/255 |
| 0071227 | 2/1983 | European Pat. Off. | 536/24 |
| 0007486 | 7/1962 | Japan | 544/255 |
| PCT/US/01-722 | 11/1983 | World Int. Prop. O. | |
| PCT/US/02-716 | 12/1986 | World Int. Prop. O. | |

OTHER PUBLICATIONS

Kochetkov et al., "Organic Chemistry of Nucleic Acids", Part B, Plenum Press, New York, 1972, pp. 449–465.

Primary Examiner—Ronald W. Griffin
Assistant Examiner—L. Eric Crane
Attorney, Agent, or Firm—Herb Boswell

[57] ABSTRACT

Compounds of the structure:

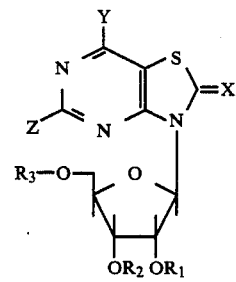

wherein $R_1$ and $R_2$ individually are H or $C_1$-$C_{18}$ acyl and $R_3$ is H, $C_1$-$C_{18}$ acyl or

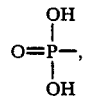

or $R_1$ is H and together $R_2$ and $R_3$ are

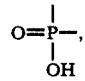

and X is =O or =S, Y is —OH, —SH, —NH$_2$ or halogen, and Z is H, —NH$_2$, —OH or halogen, wherein halogen is Cl or Br, or a pharmaceutically acceptable salt thereof are useful as antivirals, antitumors and as immune system enhancers.

17 Claims, No Drawings

ANTIVIRAL METHODS UTILIZING RIBOFURANOSYLTHIAZOLO[4,5-D]PYRIMDINE DERIVATIVES

BACKGROUND OF THE INVENTION

This invention is directed to new and improved antiviral, antitumor immune system enhancing nucleosides and nucleotides.

The immune system is an inherently complex system that serves its host by providing natural resistance and recovery against both pathogens of an external source as well as aberrant "self" cells, i.e. tumor growth. It provides both "natural", i.e. inborn and unchanging, or "acquired", i.e. adaptive immune response.

For the most part the immune system is innocuous to "self." The immune system is able, in most instances, to recognize "self," its host, and differentiate between "self" and non-self. That is the immune system is "self tolerant." In certain instances, however, the immune system does attack its host as if it was foreign resulting in autoimmunity or autoimmune disease or hypersensitivity expressed in the form of allergies, certain forms of kidney disease and the like.

While for the most part an effective and active immune system confers biological advantages for the host, modern medicine has sought in certain instances to repress the immune system because of autoimmunity hypersensitivity in graft or organ transplant and in other instances stimulate the immune system by immunization. It is therefore advantageous in certain intances to attempt to stimulate the immune system against pathogen or tumor attack and other instances to repress the immune system when it becomes self destructive to the host or for organ transplant or the like.

While most molecular entities either synthetic or natural which are known to stimulate the immune system are large molecules such as interferon, poly I:C or large messenger proteins, certain small molecules have also been shown to modulate the immune system as well. Of the small molecular entities the nucleoside 3-deaza-adenosine has been indicated in U.S. Pat. No. 4,309,419 to Walberg, et al., which issued Jan. 5, 1982, as being an inhibitor of the immune response. Other nucleosides, most notably 8-bromoguanosine, 8-mercaptoguanosine and 7-methyl-8-oxoguanosine have been noted as showing stimulation of the immune system.

Certain components of the immune system are cellular in nature while others are humoral, that is they exist free in serum or other body fluids. Adaptive immunity is based upon special properties of lymphocytes. The lymphocyte populations are generally divided between T lymphocytes commonly called T cells and B lymphocytes commonly called B cells. The T lymphocytes undergo a maturation processing in the thymus whereas the B lymphocytes are continuously generated in the bone marrow and are responsible for the production of antibodies. The lymphocytes freely circulate in the blood and from blood gain access to the tissues from which they are collected and recycled back via the lymph systems including the lymph glands and spleen.

Components of the cellular immune mechanisms include macrophages (hereinafter also refered to as MAC's), polymorphonuclear leucocytes commonly called PMN, mast cells and other cellular or molecular entities such as interferon and the like. Further, complements which are a series of proteins present in the serum can be activated by other immune components or directly by pathogens such as bacteria or the like.

Natural killer cells, hereinafter also identified as NK cells, constitute a group of cells which are concerned with natural immunity. These are lymphoid cells which are generally found in at least the young of all mammallian species and can be readily elicited in older animals. They generally exert a selective cytotoxicity against a range of target cells mostly malignant tumor cells.

The B cells produce antibody. Antibodies are a group of proteins of various classes including IgG, IgM, IgA, IgD, IgE. Not all specific antibody classes are present in different animal species. Generally the higher up on the evolutionary chain of animals the more antibody species present with warm blooded mammals generally having a full contingent of the different antibody species. The immune system is capable of modifying certain regions on the antibody proteins allowing the antibody protein to bind with specific antigens of various origins. These include pathogens, parts of pathogens such as cellular wall polysaccharide molecules, large protein or the like, as well as other foreign debris such as pollen and even in autoimmune diseases portions of the host itself. Some antibody production by the B cells is independent of the T cells while other antibody production is T cell dependent.

There are several groups of T cells including helper T cells which stimulate other T cells and B cells for the production of antibody, supressor T cells which modulate the immune response to keep it from overwhelming the host, cytotoxic T cells (CTL's) which are very important against pathogens especially viral pathogens and delayed hypersensitive T cells which are important in attracting and activating a variety of other cells, including the macrophages.

The immune system is important in protecting the host against a variety of pathogens including bacteria, viruses, protozoa, parasitic worms such as flukes, tapeworms and round worms, fungi, and tumor cells of the host which become parasitic on the host. The antiviral activity of the immune system is generally associated with the T cells whereas the natural antitumor ability of the host resides with the macrophages, the natural killer cells, certain non-T and non-B myeloid cells and with certain portions of the complement system.

As is evident, the immune system is a very complex system which is extremely important to the host for protection of the host against outside pathogens as well as against internal aberrant cells. Catastrophic effects to the host can result when pathogens, tumors or the like overwhelm the immune system of the host. It has even been suggested that tumors may have the ability to depress or subvert the hosts immune system. This is supported by the recognition of clinicians that viral and bacteria infections can be a major contributor to the deaths among tumor patients.

In view of the above it is evident that there is a need for new and improved antiviral and antitumor immune enhancing agents.

SUMMARY OF THE INVENTION

The present invention relates to a novel class of nucleosides and nucleotides of the thiazolo[4,5-d]pyrimidine ring system.

In accordance with the invention, disclosed are compounds of the formula:

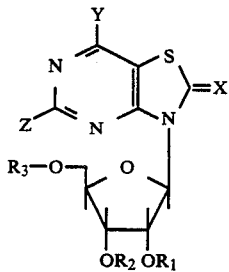

wherein $R_1$ and $R_2$ individually are H or $C_1$–$C_{18}$ acyl and $R_3$ is H, $C_1$–$C_{18}$ acyl or

or $R_1$ is H and together $R_2$ and $R_3$ are

and X is =O or =S: Y is —OH, —SH, —NH$_2$ or halogen: and Z is H, —NH$_2$, —OH or halogen, wherein halogen is Cl or Br: or a pharmaceutically acceptable salt thereof.

These compounds are useful as immune system enhancers and have certain immune system properties including modulation, mitogenicity, augmentation and/or potentiation or they are intermediates for compounds which have these properties. The compounds have been shown to express effects on at least the natural killer, macrophages and lymphocyte cells of the immune system of a host. Because of these properties they are useful as antiviral and antitumor agents or as intermediates for antiviral and antitumor agents. They can be used to treat an affected host by serving as the active ingredients of suitable pharmaceutical compositions.

In accordance with the invention, compounds of the above referenced structure are utilized to treat viral diseases in mammals by administering to the mammal a therapeutically effective amount of the compounds.

Further in accordance with the invention, compounds of the above referenced structure are utilized to treat tumors in mammals by administering to the mammal a therapeutically effective amount of the compounds.

Additionally in accordance with the invention, compounds of the above referenced structure are utilized to stimulate the immune system of a mammalian host by administering to the mammalian host a therapeutically effective amount of the compounds.

Additionally in accordance with the invention, 5-amino-3-β-D-ribofuranosylthiazolo[4,5-d]pyrimidin-2,7(6H)-dione is utilized to enhance natural killer immune cells in a host by administering to the host a therapeutically effective amount of 5-amino-3-β-D-ribofuranosylthiazolo[4,5-d]pyrimidin-2,7(6H)-dione as the active component in a pharmaceutical composition.

Additionally in accordance with the invention, 5-amino-3-β-D-ribofuranosylthiazolo[4,5-d]pyrimidin-2,7(6H)-dione is utilized to enhance macrophage cells in a host by administering to the host a therapeutically effective amount of 5-amino-3-β-D-ribofuranosylthiazolo[4,5-d]pyrimidin-2,7(6H)-dione as the active component in a pharmaceutical composition.

Additionally in accordance with the invention, 5-amino-3-β-D-ribofuranosylthiazolo[4,5-d]pyrimidin-2,7(6H)-dione is utilized to enhance lymphocyte cells in a host by administering to the host a therapeutically effective amount of 5-amino-3-β-D-ribofuranosylthiazolo[4,5-d]pyrimidin-2,7(6H)-dione as the active component in a pharmaceutical composition.

Additionally in accordance with the invention a therapeutical pharmaceutical composition is disclosed which contains as its active ingredient a therapeutically effective amount of 5-amino-3-β-D-ribofuranosylthiazolo[4,5-d]pyrimidin-2,7(6H)-dione.

Additionally in accordance with the invention a prophylactic pharmaceutical composition is disclosed which contains as its active ingredient a prophylatically effective amount of 5-amino-3-β-D-ribofuranosylthiazolo[4,5-d]pyrimidin-2,7(6H)-dione. In addition the prophylatic composition can include a further antiviral agent as a further active ingredient.

Since as antitumor agents the compounds of the invention stimulate various natural immune system responses, the compounds of the invention would be useful against a broad spectrum of tumors including but not necessary limited to carcinomas, sarcomas and leukemias. Included in such a class are mammary, colon, bladder, lung, prostate, stomach and pancreas carcinomas and lymphoblastic and myeloid leukemias.

The method of treating tumors is effective in bringing about regression, palliation, inhibition of growth and remission of tumors.

DETAILED DESCRIPTION OF THE INVENTION

The synthesis of the guanosine analog, 5-amino-3-β-D-ribofuranosylthiazolo[4,5-d]pyrimidine-2,7(6H)-dione, can be effected by the direct glycosylation of the preformed guanine base analog. (Scheme I). Thus, 5-aminothiazolo[4,5-d]pyrimidine-2,7(3H,6H)-dione (4), prepared in five steps from the commercially available diaminopyrimidinone by the method of Baker and Chatfield, J. Chem. Soc. (C), 2478 (1970), was glycosylated by trimethylsilylation using hexamethyldisilazane followed by treatment with 1-0-acetyl-2,3,5-tri-0-benzoyl-D-ribofuranose (5) in the presence of trimethylsilyl trifluoro-methanesulfonate as a catalyst. The major product, 5-amino-3-(2,3,5-tri-0-benzoyl-β-D-ribofuranosyl)thiazolo[4,5-d]pyrimidine-2,7(6H)-dione (6) was isolated.

Treatment of 6 with sodium methoxide in methanol gave the deprotected guanosine analog, 5-amino-3-β-D-ribofuranosylthiazolo[4,5-d]pyrimidine-2,7(6H)-dione (7). When 7 was deaminated with excess nitrous acid the xanthosine analog, 3-β-D-ribofuranosylthiazolo[4,5-d]pyrimidine-2,5,7(4H,6H)-trione (8) was produced. Replacement of the 5-amino group of compound 6 by a hydrogen atom was accomplished by treatment of 6 with t-butyl nitrite in tetrahydrofuran to yield 3-(2,3,5-tri-0-benzoyl-β-D-ribofuranosyl)thiazolo[4,5-d]pyrimidine-2,7(6H)-dione (9). Deprotection of 9 using sodium methoxide in methanol or methanolic ammonia provided the inosine analog, 3-β-D-ribofuranosylthiazolo[4,5-d]-pyrimidine-2,7(6H)-dione (10).

The guanosine analog, 7, was phosphorylated and the 5'-monophosphate (11) was obtained. The 3',5'-cyclic monophosphate derivative, 12, was then prepared from 11.

The preparation of the analogous 8-mercapto compound in the thiazolo[4,5-d]pyrimidine system is depicted in Scheme II starting with 5-amino-2-chlorothiazolo[4,5-d]pyrimidin-7(6H)-one (13). Compound 13 was reacted with NaSH in ethylene glycol at 110° to provide the 2-thioxo heterocycle, 14. Glycosylation of 14 by the same procedure as that used to prepare the 2-oxo compound, 6, (except that some heating was required to ensure that any S-glycoside formed would be converted to the more thermodynamically stable N-glycoside) resulted in the formation of 5-amino-2-thioxo-3-(2,3,5-tri-0-benzoyl-β-D-ribofuranosyl)thiazolo[4,5-d]pyrimidin-7(6H)-one (15). Treatment of 15 with sodium methoxide in methanol yielded the 8-mercaptoguanosine analog, 5-amino-2-thioxo-3-β-D-ribofuranosylthiazolo[4,5-d]pyrimidin-7(6H)-one (16).

Various related derivatives in the guanosine analog series were also prepared. The 6-thioguanosine analog was prepared by two routes starting from 6 (Scheme III). In one approach, 6 was treated with the mild chlorinating agent dimethyl(chloromethylene)ammonium chloride (generated in situ from thionyl chloride and DMF), and provided 5-amino-7-chloro-3-(2,3,5-tri-0-benzoyl-β-D-ribofuranosyl)thiazolo[4,5-d]pyrimidin-2-one (17). Reaction of 17 with thiourea in refluxing ethanol gave the protected thio-guanosine analog, 5-amino-7(6H)-thioxo-3-(2,3,5-tri-0-benzoyl-β-D-ribofuranosyl)thiazolo[4,5-d]pyrimidin-2-one (18). Compound 18 was also prepared directly from 6 by reaction with $P_2S_5$ in pyridine. Deprotection of 18 was accomplished either with sodium methoxide in methanol or with methanolic ammonia and the 6-thioguanosine analog, 5-amino-7(6H)-thioxo-3-β-D-ribofuranosylthiazolo[4,5,-d]pyrimidin-2-one (19) was isolated as the crystalline monohydrate. The chloro function at position 7 was also nucleophilically substituted by azide using sodium azide in dry DMF which subsequently ring closed onto N-6 to form the new tricyclic ring compound, 5-amino-7-(2,3,5-tri-0-benzoyl-β-D-ribofuranosyl)tetrazolo[1,5-c]thiazolo[4,5-d]pyrimidin-2-one (20).

In an effort to study the thiazolo[4,5-d]pyrimidine ring system with respect to the order of nucleophilic substitution at the 2,5, and 7 positions and possibly use this information to synthesize the adenosine analog, chlorinatation of the readily available 2-chlorothiazolo[4,5,-d]pyrimidine-5,7(4H,6H)-dione (21) using refluxing $POCl_3$ and N,N-dimethylaniline (Scheme IV) was effected. The desired 2,5,7-trichloro-thiazolo[4,5,-d]pyrimidine (22) was obtained along with a small amount of 5,7-dichloro-2-(N-methyl-anilino)-thiazolo[4,5-d]pyrimidine (23). The trichloro compound, 22, was carefully hydrolyzed in 1N NaOH at 60° C. in order to obtain the mono-oxo derivative, 5,7-dichloro-thiazolo[4,5-d]pyrimidin-2(3H)-one (24), the structure of which was verified by single crystal X-ray analysis. Reaction of 24 with 1,2,3,5-tri-0-acetyl-D-ribofuranose (25) under fusion glycosylation conditions produced 5,7-dichloro-3-(2,3,5-tri-0-acetyl-β-D-ribofuranosyl)thiazolo[4,5-d]pyrimidin-2-one (26). Attempts to use 26 for further modification to obtain the adenosine analog were unsuccessful due to the labile nature of the thiazole ring toward nucleophilic ring-opening.

This was circumvented by the synthesis of the adenosine analog from its preformed heterocycle in the same manner as that used to obtain the guanosine analog. The known 2,7-diaminothiazolo[4,5-d]pyrimidine (27) served as the starting material (Scheme V). Treatment of 27 with nitrous acid under conditions similar to those used to prepare 13 provided 7-amino-2-chlorothiazolo[4,5-d]pyrimidine (28). The structure of compound 28 was verified by single-crystal X-ray analysis. Treatment of 28 with NaSH in DMF at 0° C. yielded the 2-mercapto derivative, 7-aminothiazolo[4,5-d]pyrimidine-2(3H)-thione (29). The conversion of the 2-thioxo function in 29 to a 2-oxo function was accomplished using cold alkaline hydrogen peroxide to yield 7-aminothiazolo[4,5-d]pyrimidin-2(3H)-one (30). Reaction of 30 with the benzoyl-protected sugar, 5, under the same glycosylation conditions (at room temperature) as used to produce the blocked guanosine analog, 6, resulted in the formation of the unexpected blocked 4-ribofuranosyl isomer, 7-amino-4-(2,3,5-tri-O-benzoyl-β-D-ribofuranosyl)-thiazolo[4,5-d]pyrimidin-2(3H)-one (31), as the only isomer detected and isolated. If, however, the same reaction was carried out at elevated temperature (80° C.), the predominant product obtained was the desired 3-ribofuranosyl isomer, 7-amino-3-(2,3,5-tri-O-benzoyl-β-D-ribofuranosyl)-thiazolo[4,5-d]pyrimidin-2(3H)-one (32). Both isomers, 31 and 32, were deprotected using sodium methoxide in dry methanol to obtain 7-amino-4-β-D-ribofuranosylthiazolo[4,5-d]pyrimidin-2(3H)-one (33) and 7-amino-3-β-D-ribofuranosylthiazolo[4,5-d]pyrimidin-2(3H)-one (34), respectively.

For the compounds of the invention, pharmaceutically acceptable acid addition salts of the basic moiety can be selected from, but not necessarily limited to, the group consisting of hydrochloride, hydrobromide, hydroiodide, citrate, sulfate, substituted sulfate, phosphate, carbonate, bicarbonate and formate. Pharmaceutically acceptable salts of the phosphate moiety can be selected from, but not necessarily limited to, the group consisting of alkali and alkaline earths, e.g. sodium, potassium, calcium, magnesium, lithium: ammonium and substituted ammonium trialkylammonium, dialkylammonium, alkylammonium, e.g. triethylammonium, trimethylammonium, diethylammonium, octylammonium, cetyltrimethylammonium and cetylpyridium.

The hydroxyl groups on the glycon and heterocycle and the amino groups of the heterocycle can be blocked with groups such as, but not necessarily limited to, acyl, isopropylidene and dimethylaminomethylene. The acyl group can be selected from a group consisting of $C_1$–$C_{18}$ straight chain, brached chain, substituted, unsaturated, saturated or aromatic acid such as, but not necessarily limited to acetic, trifluoroacetic, propionic, n-butyric, isobutyric, valeric, caproic, pelargonic, enanthic, caprylic, lactic, acrylic, propargylic, palmitic, benzoic, phthalic, salicylic, cinnamic and naphthoic acids.

Melting points were taken on a Thomas-Hoover capillary melting point apparatus or on a Haake-Buchler digital melting point apparatus and are uncorrected. Nuclear magnetic resonance ($^1$H NMR) spectra were determined at 300.1 MHz with an IBM NR300AF spectrometer. The chemical shifts are expressed in δ values (parts per million) relative to tetramethylsilane as internal standard. Ultra violet spectra (UV: sh=shoulder) were recorded on a Beckman DU-50 spectrophotometer. Elemental analyses were performed by Robertson

EXAMPLE 1

5-amino-3-(2,3,5-tri-O-benzoyl-β-D-ribofuranosyl)-thiazolo[4,5-d]pyrimidine-2,7(6H)-dione (6)

A mixture of dry 5-aminothiazolo[4,5-d]pyrimidine-2,7(3H,6H)-dione 4 (5.5 g, 30 mmol), hexamethyldisilazane (HMDS, 100 mL), ammonium sulfate (15 mg) and pyridine (10 mL) was heated under reflux for 4 h with the exclusion of moisture. Excess HMDS was removed by distillation to provide the syrupy bis-silyl derivative. The bis-silyl intermediate was dissolved in dry acetonitrile (300 mL) and 1-O-acetyl-2,3,5-tri-O-benzoyl-D-ribofuranose (5: 15.1 g, 30 mmol) was added followed by trimethylsilyl trifluoromethanesufonate (9.3 mL, 42 mmol). The clear reaction mixture was stirred at ambient temperature for 16 h. The solvent was evaporated to dryness and the residual syrup was dissolved in EtOAc (600 mL). The solution was washed with 5% NaHCO$_3$ solution (2×150 mL), and the dried (Na$_2$SO$_4$) organic layer was evaporated. The residual syrup was triturated with ether to yield 18.1 g (96%). The resulting foam was purified on a silica gel column by Prep LC techniques using CHCl$_3$—MeOH (9:1, v/v) as the solvent. Recrystallization of the residue from EtOH gave 5-amino-3-(2,3,5-tri-O-benzoyl-β-D-ribofuranosyl)-thiazolo[4,5-d]pyrimidin-2,7(6H)-dione (6) as colorless cyrstals: yield 14.5 g, 77%: mp 248°–250° C.: UV λ$_{max}$ (pH 1) 215 sh nm (ε28000), 219 (28000), 224 sh (27600), 301 (8500): UV λ$_{max}$ (pH 7) 215 sh nm (ε28900), 222 (29500), 301 (10600): UV λ$_{max}$ (pH 11) 218 nm (ε27800), 273 (6900): Anal. Calcd. for C$_{31}$H$_2$N$_4$O$_9$S: C, 59.23: H, 3.85: N, 8.91: S, 5.10. Found: C, 59.26: H, 3.89: N, 8.93: S, 5.23.

EXAMPLE 2

5-Amino-3-β-D-ribofuranosylthiazolo[4,5-d]pyrimidine-2,7(6H)-dione (7)

A solution of 6 (0.75 g, 1 mmol) in methanol (75 mL) was adjusted to pH 9 with NaOCH$_3$ and stirred at room temperature for 16 h. The reaction mixture was evaporated to dryness and the residue was triturated with ether (2×75 mL). The ether insoluble solid was dissolved in water (15 mL) and acidified with acetic acid whereupon the crude product precipitated. Crystallization of this material from water gave a colorless powder: yield 0.31 g, 78%: mp 238° C. (decomp.): UV λ$_{max}$ (pH 1) 215 nm (ε2280), 245 (6900), 301 (8400): UV λ$_{max}$ (pH 7) 215 nm (ε22100), 245 (6900), 301 (8000): UV λ$_{max}$ (pH 11) 245 nm (ε5700), 291 (6000). NMR (DMSO-d$_6$) δ5.79 (1H, d, J=5.32 Hz, C$_1$, H), 6.90 (2H, s, NH$_2$), 11.12 (1H, s, NH), and other sugar protons. Anal. Calcd. for C$_{10}$H$_{12}$N$_4$O$_6$S.H$_2$O: C, 35.92: H, 4.22: N, 16.76: S, 9.59. Found: C, 35.82: H, 4.02: N, 16.92: S, 9.66.

EXAMPLE 3

3-β-D-Ribofuranosylthiazolo[4,5-d]pyrimidine-2,5,7(4H,6H)-trione (8)

To a suspension of 7 (0.76 g, 2.4 mmol) in glacial acetic acid (150 mL) was added dropwise a solution of sodium nitrite (1.5 g, 21.7 mmol) in water (15 mL) with stirring. After 30 min the suspension became clear and stirring was continued at room temperature overnight. The white solid which had separated was filtered, washed with cold water and dried. Recrystallization from hot water gave fine colorless crystals of 8: yield 0.3 g, 40%: mp 250° C. dec.: UV λ$_{max}$ (pH 1) 293 nm (ε5500): UV λ$_{max}$ (pH 7) 212 nm (ε14200), 301 (6100): UV λ$_{max}$ (pH 11) 204 nm (ε21900), 301 (5600). Anal. Calcd. for C$_{10}$H$_{11}$N$_3$O$_7$S: C, 37.86: H, 3.49: N, 13.24: S, 10.10. Found: C, 37.81: H, 3.42: N, 13.01: S, 10.01.

EXAMPLE 4

3-(2,3,5-Tri-O-benzoyl-β-D-Ribofuranosyl)-thiazolo[4,5-d]pyrimidine-2,7(6H)-dione (9)

To a solution of 6 (6.65 g, 10.6 mmol) in dry THF (350 mL) was added ter-butyl nitrite (6.2 mL, 52.3 mmol) and the mixture was stirred at room temperature for 1 h. Additional nitrite reagent (2.0 mL) was added and the mixture was stirred at 50°–60° C. overnight. The mixture was evaporated and the residue was purified by flash column chromatography on silica gel using 8–10% acetone in CH$_2$Cl$_2$ followed by 10–11%. The desired product eluted last to yield 3.45 g (46%) of 9 as a foam: UV λ$_{max}$ (EtOH) 220 nm (ε46600), 259 sh (11000), 271 sh (8400): $^1$H NMR (DMSO-d$_6$) δ6.31 (d, J=6.45 Hz, 1H, C$_1$, H), 7.38-7.98 (m, 15H, benzoyl aromatics), 8.25 (s, 1H, C$_5$H), 13.16 (b, 1H, N$_6$H, exchanged with D$_2$O), and other sugar protons. Anal. Calcd. for C$_{31}$H$_{23}$N$_3$O$_9$:

EXAMPLE 5

3-β-D-Ribofuranosylthiazolo[4,5-d]pyrimidine-2,7(6H)-dione (10)

Compound 9 (1.0 g, 1.63 mmol) was combined with methanolic ammonia (saturated at 0° C., 50 mL) and heated at 90° C. for 14 h in a steel bomb. The solvent was evaporated and the residue was treated with hot benzene which was decanted off. The resulting solid was purified by silica gel flash chromatography using chloroform and then CHCl$_3$—MeOH (6:1) to yield 280 mg (57%) of 10 after crystallization from water: mp 216°–218° C.: UV λ$_{max}$ (pH 1) 217 nm (ε25300), 259 (9700), 286 (6300): $^1$H NMR (DMSO-d$_6$) δ5.85 (d, J=5.1 Hz, 1H, C$_1$, H), 8.30 (s, 1H, C$_5$H), 13.09 (b, 1H, N$_6$H, exchanges with D$_2$O), and other sugar protons. Anal. Calcd. for C$_{10}$H$_{11}$N$_3$O$_6$S: C, 39.87: H, 3.68: N, 13.95: S, 10.64. 3.61: N, 14.06: S, 10.43.

EXAMPLE 6

5-Amino-3-β-D-Ribofuranosylthiazolo[4,5-d]pyrimidine-2,7(6H)-dione 5'-Monophosphate Ammonium Salt (11)

To a suspension of 7 (2.1 g, 6.6 mmol) in freshly distilled trimethyl phosphate (25 mL) at −20° C. was added POCl$_3$ (0.64 mL, 6.6 mmol) and then an additional equivalent of POCl$_3$ after 1 h. The mixture was stirred at −5° C. for another 2 h and then poured into ethyl ether (150 mL, anhydrous) and centrifuged (6000 rpm, 10 min). The ether layer was decanted and ice water (100 mL) was added to the residual oil. The pH of the resulting solution was adjusted to 7.5 with aqueous ammonium bicarbonate and the solution was applied to a DEAE-cellulose column (3.2×35 cm), washed with water and eluted with a gradient (0 to 0.25 M, 2 L reservoirs) of aqueous ammonium bicarbonate. During the water wash, unreacted starting material eluted off (0.5 g). The appropriate fractions were pooled, evaporated and lyophilized several times to yield 1.01 g (48%, based on reacted starting material): mp 190°–194° C. UV $\lambda_{max}$ (pH 1,7) 243 nm ($\epsilon$), 301 (): UV $\lambda_{max}$ (pH 11) 243 nm ($\epsilon$), 289 (): $^1$H NMR (DMSO-d$_6$) $\delta$5.71 (s, 1H, C$_1$, H), 7.15 (b, 5H, NH$_2$ and NH$_4^+$, exchanges with D$_2$O), 11.25 (b, 1H, N$_6$H, exchanges with D$_2$O), and other sugar protons. Anal. C$_{10}$H$_{14}$N$_5$O$_8$SP.1.25H$_2$O: C, 28.75: H, 3.98: N, 16.76: S, 7.67: P, 7.41. Found: C, 29.15: H, 3.68: N, 16.39: S, 7.76: P, 7.22.

EXAMPLE 7

5-Amino-3-$\beta$-D-Ribofuranosylthiazolo[4,5-d]pyrimidine-2,7(6H)-dione 3',5'-Cyclic Monophosphate Ammonium Salt (12)

Compound 11 (1.02 g, 2.28 mmol) was dissolved in water (10 mL) and pyridine (3 mL) and morpholinodicyclohexylcarbodiimide (667 mg, 2.28 mmol) was added. The solution was evaporated and co-evaporated to a syrup several times with dry pyridine. After drying overnight over P$_2$O$_5$ under vacuum, the syrup was dissolved in dry pyridine (100 mL) and added dropwise to a refluxing solution of pyridine (300 mL) containing DCC (25 g). The solution was refluxed for an additional 2 h, cooled and allowed to stir overnight. The mixture was evaporated to dryness and the residue was partitioned between water (150 mL) and ethyl ether (150 mL). The aqueous layer was concentrated to about 100 mL and applied, having pH 7.7, to a DEAE-cellulose column (3.2×30 cm) and washed with water followed by elution using a gradient of aqueous ammonium bicarbonate (0 to 0.19 M). The proper fractions were coolected based on UV monitoring, evaporated and lyophilized several times to yield 190 mg (22%) of the title compound: mp 244° C. (dec.): UV $\lambda_{max}$ (pH 1,7) 243 nm ($\epsilon$), 300 (): UV $\lambda_{max}$ (pH 11) 243 nm ($\epsilon$), 289 (): $^1$H NMr (DMSO-d$_6$) $\delta$5.60 (d, J=4.44, 1H, 2'OH, exchanges with D$_2$O), 5.72 (s, 1H, C$_1$, H), 7.15 (b, 6H, NH$_2$ and NH$_4$, exchanges with D$_2$O), 11.40 (b, 1H, N$_6$H, exchanges with D$_2$O), and other sugar protons. Anal. Calcd. for C$_{10}$H$_{11}$N$_4$O$_8$SP.NH$_3$.1.25H$_2$O: C, 28.75: H, 3.98: N, 16. Found: C, 29.15: H, 3.68: N, 16.39: S, 7.76: P, 7.22.

EXAMPLE 8

5-Amino-2-thioxothiazolo[4,5-d]pyrimidin-7(6H)-one (14)

A suspension of 5-amino-2-chlorothiazolo[4,5-d]pyrimidin-7(6H)-one (13: 1.5 g, 7.4 mmol) in ethylene glycol (30 mL) was heated to 110° C. and NaSH$_x$H$_2$O (420 mg, 74 mmol) was added. A clear solution was not obtained, however, until an additional 250 mg were added. The clear solution was stirred at 110° C. for 2 h and then the reaction mixture was cooled to room temperature, poured into ice (300 mL), and the pH adjusted to 2–3 with 10% HCl. The resulting pink gelatinous mixture was boiled for 1 h and the pink solid was collected by filtration through a medium frit-glass filter, washed with water and dried: yield 1.2 g, 81%: an analytical sample was prepared by flash column chromatography using EtOAc—MeOH—H$_2$O-acetone (7:1:1:1). mp >300° C.: UV $\lambda_{max}$ (pH 1) 243 nm ($\epsilon$13700), 266 (16500), 351 (17200): UV $\lambda_{max}$ (pH7) 262 nm ($\epsilon$14800), 345 (12700): UV $\lambda_{max}$ (pH 11) 250 nm ($\epsilon$19300), 335 (14300): $^1$H NMR (DMSO-d$_6$) $\delta$6.91 (s, 2H, NH$_2$), 11.18 (s, 1H, N$_6$H), 13.78 (s, 1H, N$_3$H). Anal. Calcd. for C$_5$H$_4$N$_4$OS$_2$:

EXAMPLE 9

5-Amino-2-thioxo-3-(2,3,5-tri-O-benzoyl-$\beta$-D-ribofuranosyl)thiazolo[4,5-d]pyrimidin-7(6H)-one (15)

Compound 14 (1.0 g, 5 mmol) was glycosylated in the same manner as that used to prepare 6, requiring HMDS (20 mL), benzoyl-blocked sugar (5: 2.52 g, 5 mmol), and TMS-triflate (1.45 mL, 7.5 mmol). At the end of the 16 h reaction period, the reaction mixture was heated at 70° C. for 3 h in order to rearrange any S-glycoside formed to the more stable N-glycoside. After the same workup, 15 (2.1 g crude) was purified by flash column chromatography using hexanes-acetone (1:1) and crystallized from toluene-EtOAc: yield 1.9 g, 59%: mp 230°–233° C. (darkens 195° C.). Anal. Calcd. for C$_{31}$H$_{24}$N$_4$O$_8$S$_2$: C, 57.76: H, 3.75: N, 8.69: S, 9.95. Found: C, 57.98: H, 3.46: N, 8.40: S, 9.66.

EXAMPLE 10

5-Amino-2-thioxo-3-$\beta$-D-ribofuranosylthiazolo[4,5-d]pyrimidin-7(6H)-one (16)

To a solution of 15 (1.25 g, 1.94 mmol) in dry methanol (100 mL) was added sodium methoxide powder until the pH reached 10. The solution was stirred overnight and then neutralized with Dowex H$^+$ resin and filtered. After evaporation of the filtrate, the residue was washed with ether to remove methyl benzoate and the crude material was crystallized from water: yield 520 mg, 81%: mp 220° C. dec.: UV $\lambda_{max}$ $^1$H NMR (DMSO-d$_6$) $\delta$6.48 (d, J=3.00 Hz, 1H, C$_1$, H), 6.99 (s, 2H, NH$_2$), 11.47 (s, 1H, NH), and other sugar protons. Anal. Calcd. for C$_{10}$H$_{12}$N$_4$O$_5$S$_2$.H$_2$O: C, z34.28: H, 4.03: N, 15.99: S, 18.30. Found: C, 33.99: H, 3.92: N, 15.68: S, 18.22.

EXAMPLE 11

5-Amino-7-chloro-3-(2,3,5-tri-O-benzoyl-$\beta$-D-ribofuranosyl)thiazolo[4,5-d]pyrimidin-2-one (17)

Dry purified 6 (10 g, 16 mmol) was dissolved in dry methylene chloride (350 mL) and a solution of freshly distilled thionyl chloride (40 mL), dry DMF (20 mL), in dry methylene chloride was added dropwise over a 2 h period and the reaction was kept at 60° C. (reflux) for 16 h. The reaction mixture was poured carefully into ice and NaHCO$_3$ slutio and stirred for 30 min. The layers were separated and the aqueous layer extracted (2×150 mL) with methylene chloride and the combined layers dried over Na$_2$SO$_4$ and evaporated in vacuo. The residual syrup was purified by passing throgh a silica gel column (4×40 cm) and eluting with CHCl$_3$-acetone (4:1), to obtain the chloro compound as a white foam, 8.6 g, 84%: mp 88°–90° C.: Anal. Clcd. for C$_{31}$H$_{23}$C$_1$N$_4$O$_8$S: C, 57.54: H, 3.58: Cl, 5.47: N, 8.66: S, 4.96. Found: C, 58.06: H, 3.99: Cl, 5.95: N, 9.41: S, 4.75.

EXAMPLE 12

5-Amino-7(6H)-thioxo-3-(2,3,5-tri-O-benzoyl-$\beta$-D-ribofuranosyl)thiazolo[4,5-d]pyrimidin-2-one (18)

Method 1 A mixture of 17 (3.3 g, 5 mmol), thiourea (0.719 g, 1 mmol) and EtOH (100 mL) was heated under reflux for 6 days. The reaction mixture was evaporated, and the residue was extracted with CHCl$_3$ (200 mL). The solvent was evaporated to dryness in vacuo, and the residue was purified by silica gel column chromatography with CHCl$_3$-acetone (7:1) as the eluant. After evaporation the residue was crystallized from EtOH to afford a colorless powder: yield 1.9 g, 58%: mp 227°–229° C.: UV $\lambda_{max}$ (pH 1) 234 nm ($\epsilon$26000), 280 sh (9000), 365 (11800): UV $\lambda_{max}$ (pH 11) 230 nm ($\epsilon$40500), 267 (8700), 327 (14100): Anal. calcd. for $C_{31}H_{24}N_4O_8S_2$: C, 57.75: H, 3,75: N, 8.69: S, 9.95. Found: C, 57.79: H, 3.79: N, 8.69: S, 9.98.

Method 2 To a solution of 6 (1 g, 1.6 mmol) in pyridine (50 mL) was added with stirring $P_2S_5$ (1.5 g, 6.2 mmol). The solution was refluxed gently (bath temperature 130–140) for 29 h. The reaction mixture was evaporated to dryness in vacuo. The excess $P_2S_5$ was decomposed by the addition of $H_2O$ (200 mL) at 60° C. The mixture was stirred for 1 h, then left at room temperature overnight. The resulting solid was filtered, dissolved in $CHCl_3$, dried ($Na_2SO_4$) and the solvent removed under vacuum. The residue was purified by silica gel column chromatography with $CHCl_3$-acetone 7:1 as the eluant. After concentration the residue was crystallized from EtOH to give 18 (0.43 g, 43%). The physicochemical properties of compound 18 prepared by Method 2 were found to be identical in all respects to those of the compound prepared by Method 1 above.

EXAMPLE 13

5-Amino-7(6H)-thioxo-3-$\beta$-D-ribofuranoxyl-thiazolo[4,5-d]pyrimidin-2-one (19).

Method 1 A solution of 18 (1 g, 1.6 mmol) in methanol (50 mL) was adjusted to pH 9 with $NaOCH_3$ and stirred at room temperature for 16 h. The reaction mixture was evaporated to dryness and the residue was triturated with ether (2×75 mL). The ether insoluble solid was dissolved in water (15 mL) and acidified with acetic acid whereupon the crude product was precipitated. Recrystallization of this material from EtOH-$H_2O$ gave colorless prisms: yield 0.47 g, 87%: mp 185°–187° C.: UV $\lambda_{max}$ (pH 1) 214 nm ($\epsilon$2700), 230 sh (14000), 263 (6700), 354 (): UV $\lambda_{max}$ (pH 7) 213 nm ($\epsilon$25900), 247 (9100), 266 sh (7700), 334 (12100), 353 (11800): UV $\lambda_{max}$ (pH 11) 247 nm ($\epsilon$12300), 266 sh (8800), 327 (16100): $^1$H NMR (DMSO-$d_6$) $\delta$5.76 (d, J=5.32 Hz, $C_1$, H), 7.22 (s, 2H, $NH_2$), 12.41 (s, 1H, NH), and other sugar protons. Anal. Calcd. for $C_{10}H_{12}N_4O_5S_2.H_2O$: C, 34.28: H, 4.03: N, 15.99: S, 18.30. Found: C, 34.28: H, 3.99: N, 16.24: S, 18.51.

Method 2 A solution of 18 (1.0 g, 1.6 mmol) in methanolic ammonia (saturated at 0° C., 60 mL) was stirred at room temperature for 48 h. The solvent was evaporated to dryness and the residue was triturated with boiling benzene (2×100 mL). The benzene insoluble solid was crystallized from EtOH—$H_2O$ to give 19 (0.36 g, 67%). The compound prepared by this method was identical to compound 19 prepared by Method 1 above, as judged by spectral and physical data.

EXAMPLE 14

5-Amino-7-(2,3,5-tri-O-benzoyl-$\beta$-D-ribofuranosyl)tetrazolo[1,5-c]thiazolo[4,5-d]pyrimidin-2-one (20).

To a solution of 17 (3.0 g, 4.6 mmol) in dry DMF (30 mL) was added sodium azide (0.3 g, 4.6 mmol) and the mixture was stirred at room temperature for 3 days. After evaporation of the solvent, the residue was dissolved in EtOAc (250 mL) and washed with water (2×50 mL), dried over sodium sulfate and evaporated. The resulting foam was purified by silica gel column chromatography using $CHCl_3$-acetone 7:1. The product was crystallized from EtOH to give a white powder: yield, 2.0 g, 67%: mp 112°–114° C.: IR showed no azide band in the region of 2100 to 2200 cm$^{-1}$; UV $\lambda_{max}$ (MeOH). Anal. Calcd. for $C_{31}H_{23}N_7O_8S$: C, 56.96: H, 3.55: N, 15.00: S, 4.91. Found: C, 57.19: H, 3.88: N, 15.26: S, 4.75.

EXAMPLE 15

2,5,7-Trichlorothiazolo[4,5-d]pyrimidine (22)

A mixture of 2-chlorothiazolo[4,5-d]pyrimidine-5,7(4H,6H)-dione (21, 15.8 g, 78 mmol), $POCl_3$ (220 ml) and N,N-dimethylaniline (12.3 g, 0.1 mmol) was refluxed for 3 h. The excess $POCl_3$ was removed under reduced pressure and the residue was poured into ice-water (500 mL) with stirring. The resulting aqueous solution was extracted with $CHCl_3$ (3×400 mL) and the organic layer was washed with water (2×400 mL), 0.1N NaOH (2×300 mL) and water (2×400 mL) successively and then dried over $Na_2SO_4$. Evaporation of the chloroform produced a residue which was purified by silica gel column chromatography using $CHCl_3$ to provide the title compound (22) after crystallization from EtOH. Yield 13.8 g, 74%: mp. 121°–122° C.: UV $\lambda_{max}$ (pH 1, 7, 11) 296 nm ($\epsilon$10,800). Anal. Calcd. for $C_5Cl_3N_3S$: C, 24.97: Cl, 44.22: N, 17.48. Found: C, 25.02: Cl, 44.39: N, 17.37.

EXAMPLE 16

5,7-Dichlorothiazolo[4,5-d]pyrimidin-2(3H)-one (24)

A suspension of the trichloro compound (22: 3.0 g, 12 mmol) in 1N NaOH (35 mL) was heated at 60° C. for 1 h. The solution was treated with decolorizing carbon and then acidified with 10% aqueous HCl. The resulting precipitate was collected and reprecipitated from dilute base with glacial acetic acid to provide 24 as orange needles (1.38 g, 50%): mp. 191°–192° C.: UV $\lambda_{max}$ (pH 1) 254 nm ($\epsilon$5,300), 290 (11,400): UV $\lambda_{max}$ (pH 7, 11) 226 nm ($\epsilon$28,900), 300 (14,100). Anal. Calcd. for $C_5HCl_2N_3OS$: C, 27.04: H, 0.45: Cl, 31.93: N, 18.93. Found: C, 26.78: H, 0.61: Cl, 32.15: N, 18.66. Single crystal X-ray analysis of 24 showed the structure assignment to be correct.

EXAMPLE 17

5,7-Dichloro-3-(2,3,5-tri-O-acetyl-$\beta$-D-ribofuranosyl)-thiazolo[4,5-d]pyrimidin-2-one (26)

A finely powdered mixture of 24 (3.7 g, 16 mmol), 1,2,3,5-tetra-O-acetyl-D-ribofuranose (5.3 g, 16 mmol) and bis(p-nitrophenyl)phosphate (20 mg) was heated at 170° C. for 10 min under reduced pressure. After cooling to room temperature the brown solid mass was dissolved in EtOAc (500 mL) and washed with saturated aqueous sodium bicarbonate (3×300 mL). The dried ($Na_2SO_4$) organic layer was evaporated to yield a syrup which was purified by silica gel column chromatography (4×40 cm) using toluene-EtOAc (5:1). The resulting syrup was crystallized from ethanol to give a colorless powder: yield 6.4 g, 80%: mp 125°–126° C.: $^1$H NMR (DMSO-$d_6$) $\delta$1.99, 2.06, 2.08 (3s, 9H, acetyl), 6.07 (d, J=3.40 Hz, 1H, $C_1$,H), and other sugar protons. Anal. Calcd. for $C_{16}H_{15}Cl_2N_3O_8S$: C, 40.01: H, 3.15: Cl, 14.76: N, 8.75: S, 6.68. Found: C, 40.20: H, 3.31: Cl, 14.79: N, 8.61: S, 6.66.

EXAMPLE 18

7-Amino-2-chlorothiazolo[4,5-d]pyrimidine (28)

To a suspension of 2,7-diaminothiazolo[4,5-d]pyrimidine (27: 16.3 g, 97.3 mmol) in water (200 mL) at 55° C.

was added enough 1N NaOH (about 100 mL) to dissolve the starting material and sodium nitrite (8.0 g) was then added. This solution was then added dropwise over 30 min. to a solution containing con HCl (400 mL), water (100 mL) and LiCl (60 g) at 30° C. The resulting mixture was warmed to 45° C. for 15 min. and then hot water (1 L, 90°) was added. The reaction mixture was stirred overnight at room temperature, filtered to remove unreacted starting material and the filtrate was neutralized with solid NaOH to pH 4. The resulting solid was filtered off, washed with water and dried to yield 28: 5.38 g, 34%: recrystallization from water gave an analytical sample- mp >234° C. decomp.: UV $\lambda_{max}$ (pH 1) 228 nm ($\epsilon$), 296 (): UV $\lambda_{max}$ (pH 7) 232 nm ($\epsilon$), 298 (): UV $\lambda_{max}$ (pH 11) 227 nm ($\epsilon$), 300 (): $^1$H NMR (DMSO-d$_6$) $\delta$7.82 (b, 2H, NH$_2$, exchanges with D$_2$O), 8.41 (s, 1H, C$_5$H). Anal. Calcd. for C$_5$H$_3$N$_4$SCl.0.1H$_2$O: C, 31.87: H, 1.71: N, 29.74: S, 17.02: Cl, 18.82. Found: C, 31.71: H, 1.50: N, 29.35: S, 16.92: Cl, 19.54.

EXAMPLE 19

7-Aminothiazolo[4,5-d]pyrimidine-2(3H)-thione (29)

A suspension of compound 28 (1.11 g, 5.9 mmol) in dry DMF (10 mL) was cooled in an ice bath to 0° C. and NaSH$_x$H$_2$O (0.87 g, 11.8 mmol) was added. The resulting clear solution was stirred overnight at 0° C. and then at room temperature for 2 h. The reaction mixture was poured into ice (300 mL) and the pH adjusted to 3–4 with glacial acetic acid. The solid precipitate was filtered, washed with water and dried to yield 0.96 g (88%). An analytical sample was prepared by crystallization from DMF-water: mp >370° C.: UV $\lambda_{max}$ (pH 1) 248 nm ($\epsilon$), 263 (), 345 (): UV $\lambda_{max}$ (pH 7, 11) 228 nm ($\epsilon$), 258 (), 329 (): $^1$NMR (DMSO-d$_6$) $\delta$7.57 (b, 1H, NH$_2$, exchanges with D$_2$O), 8.23 (s, 1H, C$_5$H), 14.13 (b, 1H, N$_3$H, exchanges with D$_2$O). Anal. Calcd. for C$_5$H$_4$N$_4$S$_2$: C, 32.60: H, 2.19: N, 30.41: S, 34.81. Found: C, 32.97: H, 2.13: N, 30.29: S, 34.59.

EXAMPLE 20

7-Aminothiazolo[4,5-d]pyrimidin-2(3H)-one (30)

To a suspension of 29 (770 mg, 4.2 mmol) in water (30 mL) was added 1N NaOH (4.2 mL) and 30% H$_2$O$_2$ (1.0 mL) and the reaction was stirred for 1 h at room temperature. Additional peroxide (2.0 mL) and hydroxide (5.0 mL) were added and the mixture was stirred for 1 h at 70° C. The reaction mixture was filtered and the filtrate was neutralized with glacial acetic acid. The resulting precipitate was filtered off while still hot, washed with cold water and dried to yield 0.52 g (74%): mp >370 ° C.: UV $\lambda_{max}$ (pH 1) 267 nm ($\epsilon$), 289 (): UV $\lambda_{max}$ (pH 7, 11) 285 nm ($\epsilon$): $^1$H NMR (DMSO-d$_6$) $\delta$7.18 (b, 2H, NH$_2$, exchanges with D$_2$O), 8.12 (s, 1H, C$_5$H), 12.30 (b, 1H, N$_3$H, exchanges with D$_2$O). Anal. Calcd. for C$_5$H$_4$N$_4$OS: C, 35.71: H, 2.40: N, 33.31: S, 19.07. Found: C, 35.50: H, 2.36: N, 33.13: S, 18.79.

EXAMPLE 21

7-Amino-4-(2,3,5-tri-O-benzoyl-$\beta$-D-ribofuranosyl)-thiazolo[4,5-d]pyrimidin-2-one (31)

Compound 30 (460 mg, 2.7 mmol) was glycosylated in the same manner as that used to prepare 6, requiring HMDS (30 mL), benzoyl-blocked sugar (5: 1.5 g, 3.0 mmol), and TMS-triflate (0.76 mL, 3.9 mmol). The reaction mixture was allowed to stir overnight at room temperature and was then worked up as described for 6 to yield 1.6 g (95%) of 31 isolated as a foam: UV $\lambda_{max}$ MeOH) 230 nm ($\epsilon$), 310 (): $^1$H NMR (DMSO-d$_6$9 $\delta$6.45 (d, J=2.73 Hz, 1H, C$_1$,H), 7.4–8.0 (m, 15 H, benzoyl aromatics), 8.59 (s, 1H, C$_5$H), and other sugar protons C$_{31}$H$_{24}$N$_4$O$_8$S: C, 60.78: H, 3.95: N, 9.15: S, 5.23. Found:

EXAMPLE 22

7-Amino-3-(2,3,5-tri-O-benzoyl-$\beta$-D-ribofuranosyl)-thiazolo[4,5-d]pyrimidin-2-one (32)

Compound 30 (1.22 g, 7.25 mmol) was glycosylated as described for the preparation of 6, requiring HMDS (35 mL), benzoyl-blocked sugar (5: 4.4 g, 8.7 mmol) and TMS-triflate (2.0 mL, 10.3 mmol). After stirring overnight at room temperature, the reaction mixture was refluxed for 2 days and then worked up in the usual manner. The crude mixture was subjected to flash silica gel column chromatography using a gradient of methylene chloride to methylene chloride-acetone 10:1 (v/v) and yielded two products. The first to elute from the column was assumed by $^1$H NMR to be a bis-glycoside which amounted to 660 mg. The second and major product off the column was obtained as a foam and assigned as the desired 3-ribosyl isomer by UV and $^1$H NMR: yield 1.04 g (24%): UV $\lambda_{max}$ (EtOH) 232 nm ($\epsilon$), 283 (): 1H NMR (DMSO-d$_6$) $\delta$6.34 (t, 1H, C$_1$,H), 7.39–7.98 (m, 17H, benzoyl aromatics and NH$_2$, 8.19 (s, 1H, C$_5$H), and other sugar protons. Anal. Calcd. for C, 60.78: H, 3.95: N, 9.15: S, 5.23. Found: 3.93: N, 8.13: S, 4.85.

EXAMPLE 23

7-Amino-4-$\beta$-D-ribofuranosylthiazolo[4,5-d]pyrimidin-2-one (33)

Compound 31 (310 mg, 0.51 mmol) was dissolved in dry methanol (35 mL) and cooled to 5° C. To this solution was added solid sodium methoxide (82 mg, 1.5 mmol) and the solution was stirred at room temperature for 5 h. The mixture was neutralized with Dowex-50 H+ resin, filtered and evaporated to dryness. The residue was triturated with ethyl ether and then recrystallized from aqueous ethanol to yield colorless needles: 120 mg, 80%: mp 132°–134° C.: UV $\lambda_{max}$ (pH 1) 227 nm ($\epsilon$17230), 301 (15750): UV $\lambda_{max}$ (pH 7, 11) 233 nm ($\epsilon$22300), 305 (19100): $^1$H NMR (DMSO-d$_6$) $\delta$5.96 (d, J=3.51 Hz, 1H, C$_1$,H), 7.75 (b, 2H, NH$_2$), and other sugar protons. Anal. Calcd. for C$_{10}$H$_{12}$N$_4$O$_5$S.O.2H$_2$O: C, 35.71: 9.53. Found: C, 35.45: H, 4.88: N, 16.44: S, 9.50.

EXAMPLE 24

7-Amino-3-$\beta$-D-ribofuranosylthiazolo[4,5-d]pyrimidin-2-one (34)

Compound 32 (0.76 g, 1.2 mmol) was deblocked in the same manner as described for 31 above using sodium methoxide (200 mg, 3.7 mmol) in dry MeOH (50 mL). The title compound (34) was obtained (0.12, 32%) after crystallization from water: mp 248°–250° C.: UV $\lambda_{max}$ (pH 1) 222 nm ($\epsilon$35100), 265 (14300), 290 (11400): UV $\lambda_{max}$ (pH 7, 11) 215 nm ($\epsilon$45000), 262 (13200): $^1$H NMR (DMSO-d$_6$) $\delta$5.91 (d, J=5.43 Hz, 1H, C$_1$,H), 7.44 (b, 1H, NH$_2$), 8.22 (s, 1H, C$_5$H), and other sugar protons. Anal. Calcd. for C$_{10}$H$_{12}$N$_4$O$_5$S: C, 40.00: H, 4.03: N, 18.66: S, 10.68. Found: C, 39.80: H, 3.99: N, 18.39: S, 10.57.

SCHEME I
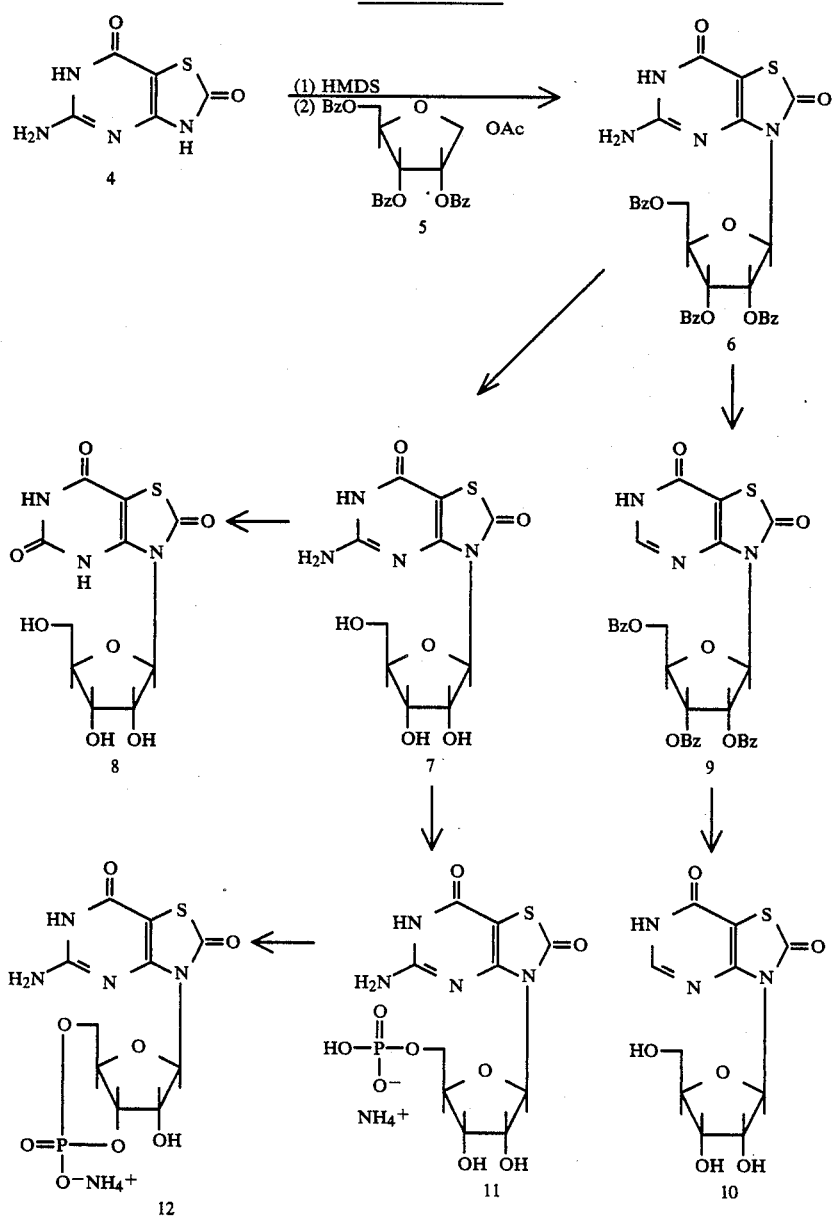
SCHEME II
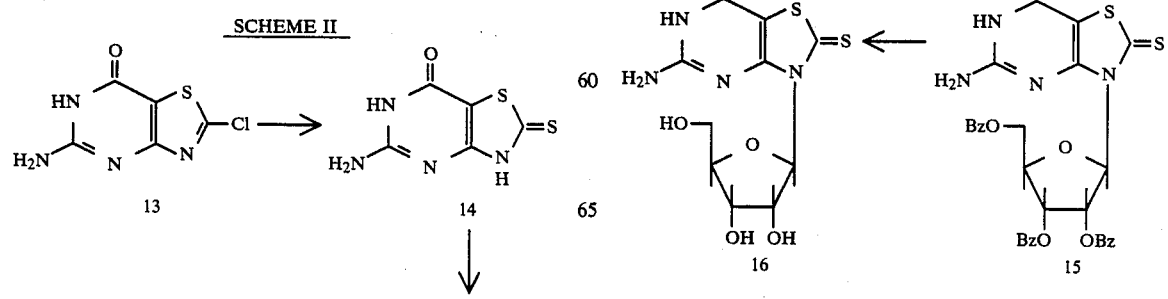

SCHEME III
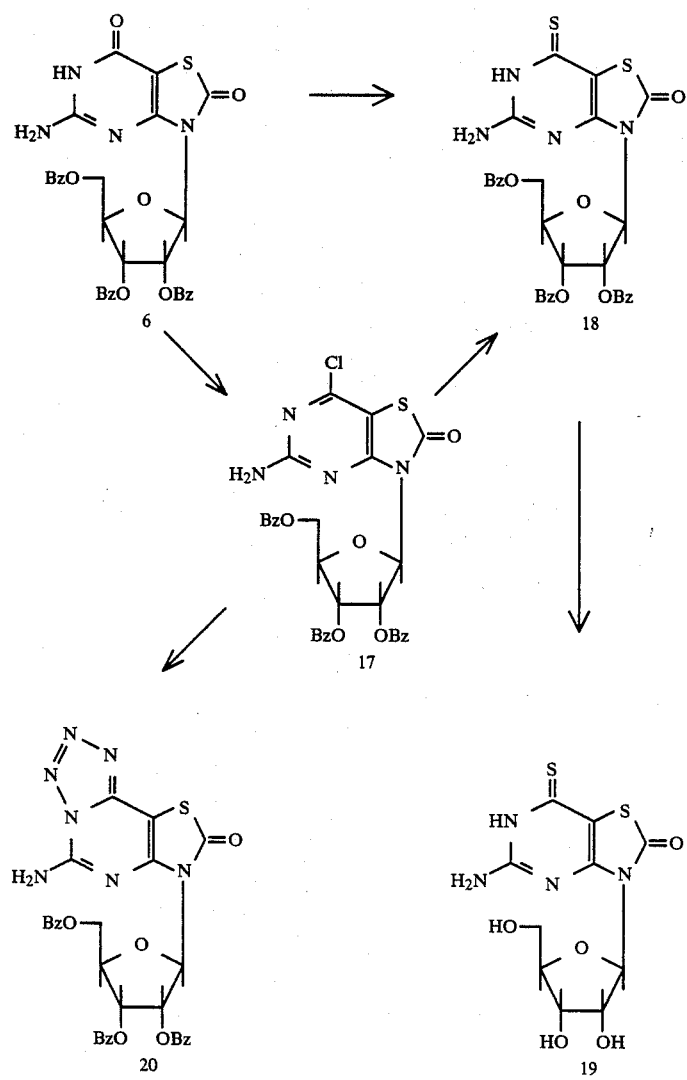
SCHEME IV
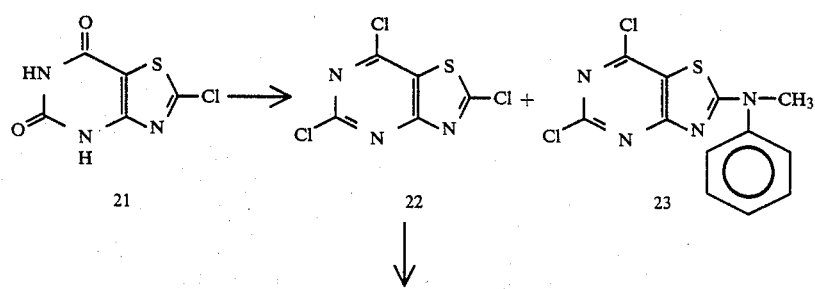

19  4,880,784  20
-continued
SCHEME IV
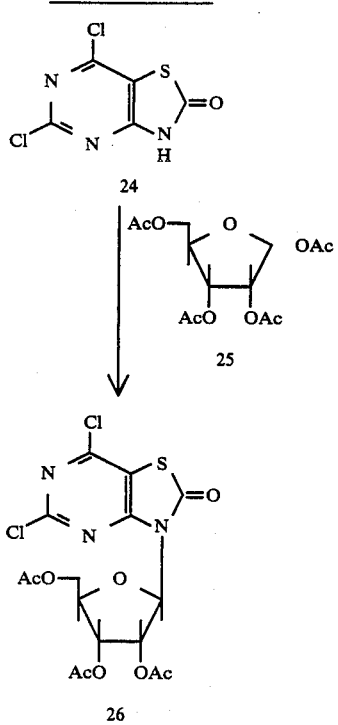
SCHEME V
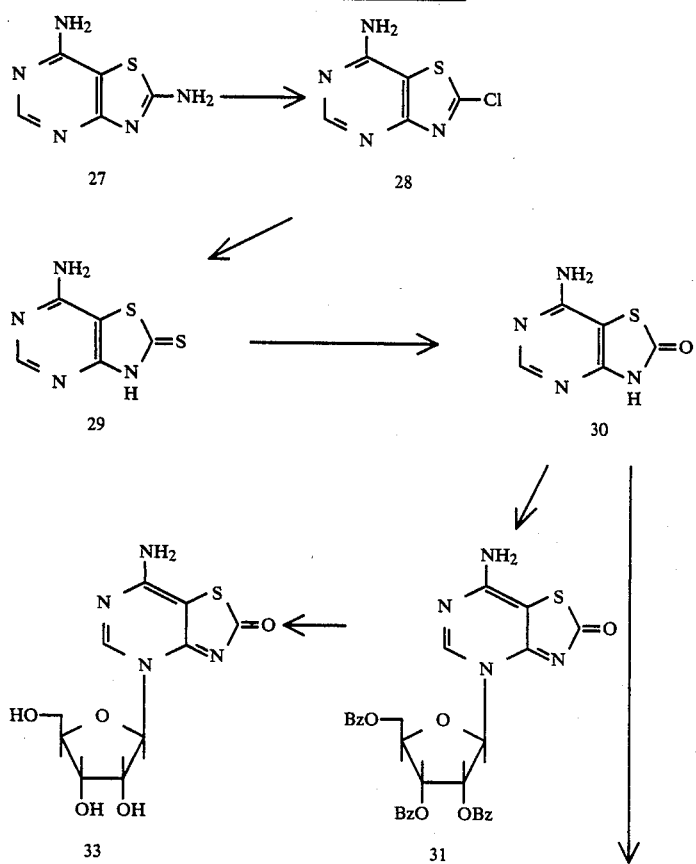

SCHEME V

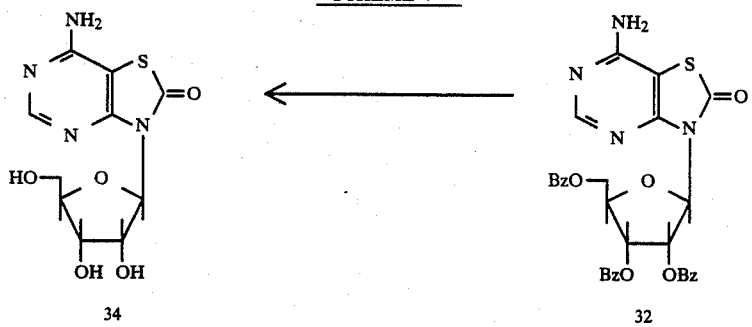

Natural killer cells have been implicated as providing defense against viral infections and malignant cells. Abnormalities in the natural killer cell's activity may thus result in the development of the diseases. Biological immunomodulators may restore or correct certain deficient immune functions. Recently interleukin-2 has been shown to have immunotherapeutic potential in tumor patients. Interleukin-2 and other known immunopotentiators are generally protein in nature and may cause severe side effects upon their administration. Non toxic low molecular synthetic compounds which are not proteins can be suggested for avoiding the side effects of known protein immuno therapeutic potentiators.

EXAMPLE 25
In Vitro Induced Potentiation of Natural Killer Cell Activity

The non protein nucleoside and nucleotide compounds of the invention have shown increased natural killer cell activity. In this example, natural killer cell activity is demonstrated in mice.

Spleen cells from CBA/CaJ or C57BL/6J mice were cultured with 0.05 mM concentrations of compound 7 for 20 to 44 hours at 37° C. in a 5% $CO_2$ humidified atmosphere as described in Djeu, J-Y, Heinbaugh, J. A., Holden, H. T., Herberman R. B.: *Journal Immunology* 122: 175, 1979, and Gonazles, H., Karriger, K., Sharma, B., Vaziri, N.: *Federal Procedures* 42: 1195, 1983. After incubation the cytotoxicity of the treated and untreated cells was determined against YAC-1 cells. In performing this test both a non-drug control and a control using Poly I:C were run concurrently with compound 7.

TABLE 1

In Vitro Induced Potentiation of Natural Killer cell Activity[a]

| Effector Cells | | % Natural Killer Cell Cytotoxicity Treatment Time (Hour) | | |
|---|---|---|---|---|
| From: | Treatment With: | 0 | 20 | 44 |
| CBA/CAJ | None | 13 | 4 | 0.5 |
| | Compound 7 | 15 | 34 | 31 |
| | Poly I:C | 14.5 | 18 | 19 |
| CBA/CAJ | None | 14 | 8 | 1 |
| | Compound 7 | 23 | 62 | 44 |
| | Poly I:C | 22 | 31 | 9 |
| C57BL/6J | None | 16 | 1.5 | 2.5 |
| | Compound 7 | 18 | 35 | 34 |
| | Poly I:C | 18 | 13 | 14 |
| C57BL/6J | None | 30 | 1.6 | 1.3 |
| | Compound 7 | 18 | 25 | 22 |

TABLE 1-continued

In Vitro Induced Potentiation of Natural Killer cell Activity[a]

| Effector Cells | | % Natural Killer Cell Cytotoxicity Treatment Time (Hour) | | |
|---|---|---|---|---|
| From: | Treatment With: | 0 | 20 | 44 |
| | Poly I: | 22 | 6 | 13 |

[a]Spleen cells from mice were treated with 0.05 mM concentration of compound 7 in RPMI-1640 medium containing 10% FCS, 0.1 mM nonessential amino acids and 5 × $10^{-5}$ M Mercaptoethanol. The effector cells were then tested for their cytotoxic activity against YAC-1 target cells in 4 hr $^{51}$Cr release assay.

As is evident from Table 1 incubation for 20 hours with compound 7 augmented natural killer cell cytotoxicity compared 4, 8, 1.5 and 1.6% for untreated control to 34, 62, 35 and 25% respectively. Similar treatment for up to 44 hours also caused a distinct increase in natural killer cell activity. Using Poly I:C as a further control, which is a well known potentiator of natural killer cells, compound 7 demonstrated increased activity compared to Poly I:C. The results of Table 1 demonstrate compound 7 markedly induces a high increase in murine natural killer cell activity.

EXAMPLE 26
In Vitro Augmentation of Human Natural Killer Cell Activity

The natural killer cell activity in human cells was also measured. In conducting these tests peripheral blood mononuclear cells (PBMNC) were isolated on Ficoll-Hypague gradient, washed three times in Hanks and re-suspended in RPMI-1640 containing 10% human AB serum as described in Rosenberg, S. A.: *Journal American Medical Association,* 256: 3117, 1986 and the above referred to reference to Djeu, et al. Peripheral blood mononuclear cells (PBMNC) from eleven different donors were treated with compound 7 as described in Djeu, et al. as well Sharma, B., Odom, L. F.: *Cancer Immunol. Immmunother.* 7: 93, 1979, and Sharma, B., Odom, L. F.: *Cancer Research* 44: 3258, 1984.

The PBMNC cells were incubated with compound 7 at 37° C. for 20 to 68 hours in a 5% $CO_2$ humid atmosphere and after incubation the cytotoxicity was determined against K562 tumor cells. The results are shown in Tables 2a and 2b.

TABLE 2a

In Vitro Augmentation of Human Natural Killer Cell Activity[a]

| Donor | % Natural Killer Cell Cytotoxicity | |
|---|---|---|
| | − Compound 7 | + Compound 7 |
| 1 | 26 | 91 |
| 2 | 4 | 29 |
| 3 | 22 | 54 |

TABLE 2a-continued

In Vitro Augmentation of Human Natural Killer Cell Activity[a]

| Donor | % Natural Killer Cell Cytotoxicity | |
|---|---|---|
| | − Compound 7 | + Compound 7 |
| 4 | 24 | 47 |
| 5 | 6 | 16 |
| 6 | 1 | 18 |
| 7 | 2 | 10 |
| 8 | 13 | 22 |
| 9 | 6 | 15 |
| 10 | 14 | 20 |
| 11 | 11 | 32 |

[a]Peripheral blood mononuclear cells were treated with 0.05–0.4 mM cencentration of compound 7 in RPMI-1640 containing 10% human AB serum for 20 to 68 hours. After the treatment, effector cells were tested against E562 target cells in 4 hour $^{51}Cr$ release assay as described in Sharma et al. above. The data shown here represent the maximum response.

TABLE 2b

In Vitro Augmentation of Human Natural Killer Cell Activity[a]

| | % Natural Killer Cell Cytotoxicity | | | |
|---|---|---|---|---|
| | Donor 1 | | Donor 2 | |
| Exp. # | − Compound 7 | + Compound 7 | − Compound 7 | + Compound 7 |
| 1 | 25 | 47 | 4 | 29 |
| 2 | 26 | 91 | 15 | 37 |
| 3 | 9 | 36 | 19 | 37 |
| 4 | 23 | 55 | 3 | 26 |
| 5 | 32 | 67 | 4 | 13 |
| 6 | 12 | 30 | 2 | 10 |
| 7 | 16 | 50 | | |
| 8 | 31 | 40 | | |

[a] Peripheral blood mononuclear cells were treated with 0.05–0.4 mM cencentration of compound 7 in RPMI-1640 containing 10% human AB serum for 20 to 68 hours. After the treatment, effector cells were tested against K562 target cells in 4 hour $^{51}Cr$ release assay as previously described above in Sharma et al. The data represent the maximum response.

As evident from Tables 2a and 2b the PBMNC from eleven donors had a mean natural killer cell cytotoxicity activity of 11.7%. The PBMNC from the same donors which was pretreated with compound 7 expressed a 32.2% mean natural killer cell cytotoxicity. While there is some variability between the eleven donors, eight of the donors showed over 100% potentiation in natural killer cell cytotoxicity. In the other four cases compound 7 treatment in vitro produced a marked increase in natural killer cell mediated cytotoxicity.

As is seen in Table 2b compound 7 also consistently mediated potentiation of the natural killer cells. In the first donor eight individual tests were run and an increase in the mediated potentiation was seen in seven of the eight tests. In the second donor the increase was seen in six of six tests. As is evident from Tables 2a and 2b compound 7 significantly induced higher levels of increase in natural killer cell activity in human cells.

In further reproducibility tests compound 7 was tested for reproducibility in its increase in natural killer cell activity as is shown in Table 2c and further for its reproducability on human natural killer cell activity as is shown in Table 2d.

TABLE 2c

Reproducibility of Compound 7 Induced Increase in Natural Killer Cell Activity

| | % Increase in Natural Killer Cell Activity | |
|---|---|---|
| | Donor | |
| Exp. # | 1 | 3 |
| 1 | 1031 | 220 |
| 2 | 658 | 102 |
| 3 | 413 | 201 |
| 4 | 200 | 66 |
| 5 | 149 | 28 |
| 6 | 460 | 136 |
| 7 | 91 | 102 |
| 8 | 98 | 200 |
| 9 | 200 | |

TABLE 2d

Effect of Compound 7 on Human Natural Killer Cell Activity

| Donor | % Increase in Induced Natural Killer Cell Activity |
|---|---|
| 1 | 1031 |
| 2 | 548 |
| 3 | 220 |
| 4 | 88 |
| 5 | 123 |
| 6 | 141 |
| 7 | 167 |
| 8 | 150 |
| 9 | 0 |
| 10 | 63 |
| 11 | 8 |

EXAMPLE 27

In Vivo Potentiation of Natural Killer Cell Activity in Mice

Compound 7 was further studied for potentiation of natural killer cell activity in vivo in mice. CBA/CaJ mice were treated with compound 7 by injecting 1.68 mg per 0.5 ml per mouse of compound 7. After 1, 2, 3 and 4 days of treatment the spleens of the mice were harvested and the cytotoxic activity of the spleen cells was determined against YAC-1 tumor target cells in the above referred to $^{51}Cr$ release assay as identified in EXAMPLE 25. The results of these tests are shown in Table 3, 4, 5 and 6.

TABLE 3

Natural Killer cell Activity in CBA/CaJ Mice[a]

| Mice CBA/CaJ | Treatment With: | Days After Treatment | % Natural Killer Cytotoxicity Effector:Target | | |
|---|---|---|---|---|---|
| | | | 50:1 | 100:1 | 150:1 |
| Group - 1 | Saline | 1 | 11 ± 3 | 18 ± 2 | 23 ± 0.3 |
| Group - 2 | Compound 7 (1.68 mg) | 1 | 53 ± 5 | 64 ± 5 | 71 ± 9 |
| Group - 3 | Compound 7 (1.68 mg) | 2 | 46 ± 9 | 64 ± 5 | 65 ± 7 |
| Group - 4 | Compound 7 (1.68 mg) | 3 | 38 ± 6.6 | 50 ± 7 | 63 ± 6 |
| Group - 5 | Compound 7 (1.68 mg) | 4 | 30 ± 0.1 | 37 ± 1.5 | 48 ± 3 |

[a]Three mice in each group were treated with saline or compound 7 (1.68 mg/mouse) by intraperitoneal route. Spleens were removed, cells were isolated and then their cytotoxicity was determined against YAC-1 target cells. Each value represents mean ±SD cytotoxic activity of three mice.

As is evident from table 3 a single injection of compound 7 at 1.68 mg per mouse caused a profound increase in natural killer cell activity. A maximum response of 382% increase was obtained one day after treatment. More than a two fold increase was observed even after 4 days with compound 7.

EXAMPLE 28

Dosage Effects on Natural Killer Cell Activity in Mice

Table 4 shows a dose response treatment with compound 7.

TABLE 4

Dosage Effects on Natural Killer Cell Activity in Mice[a]

| Mice CBA/CaJ | Treatment With: | % Natural Killer Cytoxicity Effector:Target | | |
|---|---|---|---|---|
| | | 50:1 | 100:1 | 150:1 |
| Group - 1 | Saline | 14 ± 4 | 20 ± 4 | 23 ± 3.5 |
| Group - 2 | Compound 7 (0.84 mg) | 38 ± 7 | 48 ± 9 | 56 ± 8.5 |
| Group - 3 | Compound 7 (1.68 mg) | 44 ± 8 | 56 ± 12 | 61 ± 14 |
| Group - 4 | Compound 7 (2.52 mg) | 48 ± 6.6 | 62 ± 7 | 70 ± 5 |
| Group - 5 | Compound 7 (3.36 mg) | 48 ± 4.6 | 67 ± 10 | 74 ± 6.4 |

[a]Three mice in each group were treated with saline or compound 7 by i.p. route. Spleens were removed, cells were isolated and then their cytotoxicity was determined against YC-1 target cells. Each value represent mean ±SD cytotoxic activity of three mice.

As is evident from Table 4 mice were treated with 0.84 mg to 3.36 mg per mouse of compound 7. Although all doses of compound 7 induced a marked increase in natural killer cell activity the maximum augmentation was displayed by mice that received 3.36 mg of compound 7.

EXAMPLE 29

Natural Killer Cell Activity in Old Mice

Twelve week old C57BL/6J mice have been shown (Djeu et al. above) to exhibit little spontaneous natural killer cell activity. Table 5 shows the effect of increase of natural killer cell activity in aging mice (8 Months Old). For this test compound 7 was injected at a dose of 1.67 mg per mouse and 3.34 mg per mouse and after a day the natural killer cell activity of the spleen cells was determined.

TABLE 5

Natural Killer Cell Activity in Old Mice[a]

| Mice C57BL/6J | Treatment With | % Natural Killer Cell Cytotoxicity Effector: Target | | |
|---|---|---|---|---|
| | | 50:1 | 100:1 | 150:1 |
| Group - 1 (8 Mo. Old) | Saline | 4 | 9 | 14 |
| Group - 2 (8 Mo. Old) | Compound 7 (1.67 mg) | 14 | 19 | 23 |
| Group - 3 (8 Mo. Old) | Compound 7 (3.34 mg) | 17 | 28 | 38 |
| Group - 4 (8 Wk. Old) | Saline | 5 | 7 | 7 |
| Group - 5 (8 Wk. Old) | Compound 7 (1.67 mg) | 15 | 20 | 24 |
| Group - 6 (8 Wk. Old) | Compound 7 (3.34 mg) | 17 | 27 | 31 |

[a]Three mice in each group were treated with saline or compound 7 by i.p. route. Spleens after treatment were removed, cells were isolated and then their cytotoxicity was determined against YAC-1 target cells. Each value represent ±SD cytotoxic activity of three mice.

As is evident compound 7 showed an increase in natural killer cell activity ranging from 4% untreated to 17% treated at a 50:1 effector/target ratio. The magnitude of induction of increase was similar to that displayed by compound 7 in 8 week old mice. This low molecular weight nucleoside compound induced increases in natural killer cell activity which is as high as increases mediated by Poly I:C, LPS, Pyran or interferon as has been reported Djeu et al above.

EXAMPLE 30

Natural Killer Cell Activity in Nude/Nude Mice

Compound 7 was also able to potentiate markedly the natural killer cell activity in T cell deficient (nude/nude) mice as is shown in Table 6.

TABLE 6

Natural Killer Cell Activity in Nude/Nude Mice[a]

| Mice Nude-Nude | Treatment With | % Natural Killer Cell Cytotoxicity Effector: Target | | |
|---|---|---|---|---|
| | | 50:1 | 100:1 | 150:1 |
| Group-1 | Saline | 15 ± 5 | 25 ± 7.7 | 30 ± 11 |
| Group-2 | Compound 7 (1.67 mg) | 43 ± 12 | 56 ± 12 | 61 ± 14 |
| Group-3 | Compound 7 (3.34 mg) | 38 ± 6 | 56 ± 6 | 61 ± 12 |

[a]Three mice in each group received saline or compound 7 through i.p. route, spleens were removed on one day after the treatment, cells were isolated and then their cytotoxicity was determined against YAC-1 target cells. Each value represent average ±SD cytotoxic activity of three mice.

As is evident from table 6 compound 7 showed an effective increase of over two fold of both doses tested with respect to a saline control.

EXAMPLE 31

In Vivo Potentiation of Cytotoxic Immune Functions Against Tumor

It has been shown in Bear, H. D. Cancer Research 46: 1805, 1986, that inoculation of tumor cells into mice resulted in tumor growths with concomitant induction of antigen specific T cell mediated immune response. These induced T cells have been shown to inhibit tumor growth in vivo and to cure and/or prolong the life span of tumor bearing mice. Others have further shown that tumor specific T cell mediated immune responses can be potentiated by immunomodulators. This has been shown in the above referred to reference by Bear as well as Herberman, R. B.: Journal Biol. Resp. Modifiers 3: 527, 1984, Cheever, M. A., Greenbert, P. D., Gillis, S., Fefer, A. In: A. Fefer and A. Goldstein (eds.) pp. 127, New York, Raven Press, 1982, and Rosenberg, S. A., Journal Biol. Resp. Modifiers 3: 501, 1984.

TABLE 7

In Vivo Potentiation of Cytotoxic Lymphocytes Activity Against Mastocytoma (P815) Tumor Cells Following Injection of Tumor Cells and Drug[a]

| Mice | Inoculation With | Treated With | % Cytotoxicity Days | | | |
|---|---|---|---|---|---|---|
| | | | 3 | 5 | 7 | 9 |
| DBA/2 | P815 | Saline | 13 | 4 | 9 | 9 |
| DBA/2 | P815 | Compound 7 | 30 | 24 | 32 | 27 |
| DBA/2 | P815 | Recombinant Interleukin-2 | 25 | 21 | 25 | 20 |

[a]Ten mice in each group were inoculated with 2 × 10[6] tumor cells. After 5 hours, saline or nucleoside compound 7 solution (2 mg/mouse) was administered to each mouse. On days 3,5,7 or 9, spleen cells were isolated and their cytotoxicity was determined against P815 tumor cells as described in Gonzales and Sharma.

Compound 7 was tested to determine whether or not it can increase cytotoxic lymphocytes response against mastocytoma tumor cells. In the test mice were immunized with mastocytoma cells (P815) and after 5 hours compound 7 as a solution was given in a dose of 2 ml per mouse. Further, recombinant interleukin-2 was utilized as a control given at 50 U per mouse. The ability of spleen cells to kill tumor cells was determined following a single injection of either compound 7 or recombinant interleukin-2.

As Table 7 shows cells from mice treated with compound 7 expressed statistically significant higher cytotoxicity in the control group $p<0.05$). Similarly recombinant interleuken-2 treated mice showed higher cytotoxicity activity as compared to the control group $p<0.05$). The activity of compound 7 and recombinant interleuken-2 was essentially the same showing that compound 7 can potentiate cytotoxic immune responses against tumor cells in vivo.

EXAMPLE 32

In Vitro Potentiation of IgM Production In Human Peripheral Blood Mononuclear Cells (PBMNC)

In this example B cell potentiation is measured by measuring increases of IgM production against Staphylococcus Aureus Cowan (SAC). PBMNC cells were cultured with SAC in the absence and in the presence of compound 7. After 7 and 10 days of incubation supernatants were harvested and assessed for the presence of Igm by ELISA as described in Engvall, E.: *Methods of Enzymology* 70: 419, 1980.

TABLE 8

Effect on IgM Production By Human Peripheral Blood Mononuclear Cells In Vitro

| Exp. # | Culture | IgM (µg/ml) Day 7 | Day 10 |
|---|---|---|---|
| 1 | PBMNC alone | 40 | 372 ± 38 |
| | PBMNC + SAC | 1400 ± 282 | 2500 ± 250 |
| | PBMNC + SAC + Compound 7 (0.4 mM) | 7875 ± 883 | 13400 ± 2545 |
| | PBMNC + Compound 7 (0.4 mM) | 1500 ± 424 | 2550 ± 353 |
| 2 | B Cells Alone | 38 | |
| | B Cells + SAC | 1800 | |
| | B Cells + SAC + Compound 7 | 8350 ± 212 | |
| | B Cells + Compound 7 | 1225 ± 176 | |
| 3 | PBMNC alone | 50 | |
| | PBMNC + Compound 7 (0.2 mM) | 1710 ± 127 | |
| | PBMNC + PWM | 560 ± 84 | |
| | PBMNC + SAC | 612 ± 53 | |

[a]PBMNC or enriched B cells from normal donors were cultured alone or with *Staphylococcus Aureus Cowan* (SAC) in the absence and presence of compound 7. After incubation, supernatants were harvested and checked for IgM by ELISA.

As is evident from Table 8 SAC activated PBMNC to produce IgM in both 7 and 10 day cultures. The SAC activated PBMNC cultures which included compound 7, however, displayed a significantly greater level of IgM over a two fold increase than the cultures without compound 7. Similar increases in IgM production was also observed when enriched B cells were activated with SAC in the presence of compound 7. Compound 7 was able to induce up to 34 fold increases in IgM production. This increase is much higher than the increases induced by the known mitogen"pokeweed." The results suggests that compound 7 mediates the potentiation of SAC induced IgM in vitro human culture systems.

EXAMPLE 33

In Vitro Enhancement of Primary Anti-sheep Red Blood Cell Antibody Response

Compound 7 was tested to determine its effects on primary antibody response against sheep red blood cells in vivo. Mice (C57BL/6) in groups of 4 were injected intraperitoneally with 0.1% sheep red blood cell suspended in saline. At various times compound 7 in various concentrations was administered intraperitoneally. The results of this test are shown in Table 9.

TABLE 9

Effect on Primary Anti-Sheep Red Blood Cells Antibody Response[a]

| | Mice (C57BL/6) | SRBC | Compound 7 (mg) | PFC/$10^6$ Spleen Cells |
|---|---|---|---|---|
| I | Group-1 | + | — | 103 ± 33 |
| | Group-2 | + | 2.97 | 307 ± 156 |
| | Group-3 | + | 4.97 | 371 ± 56 |
| II | Group-1 | + | — | 81 ± 29 |
| | Group-2 | + | 2.97 | 165 ± 28 |
| | Group-3 | + | 4.95 | 467 ± 170 |
| | Group-4 | + | 4.95 | 433 ± 172 |
| III | Group-1 | + | — | 44 ± 18 |
| | Group-2 | + | 1.9 | 143 ± 140 |
| | Group-3 | + | 3.3 | 176 ± 105 |

[a]Groups of four C57BL/6 mice were injected i.p. with $6.5 \times 10^6$ SRBC and various doses of compound 7. The number of PFC to SRBC (shown as mean ± SD) were determined on day 6 as described in Cheever.

For Table 9 the number of antibody cells was determined by the modified Jerne, Nordin plaque assay as disclosed in Jerne, N. K., Nordin, A. A., *Science* 140:405, 1963. The results seen in the Table 9 shows that compound 7 induced a marked increase in the number of antibody forming cells.

Compounds of the invention have alo been tested for antiviral activity. Tests have been conducted for both the therapeutic and prophylactic effect of the compounds against a variety of both RNA and DNA viruses.

EXAMPLE 34

Antiviral Activity Against Herpes Simplex Virus Types 1 and 2

In this test Compound 7 was tested against both Herpes Simplex Type 1 Virus and Herpes Simplex Type 2 Virus. The tests were conducted as prophylactic treatments in vivo utilizing the mouse as a model. In each of these tests a placebo was utilized for control purposes. The survival time reflects survival time of those animals which succomed during the test.

TABLE 10

Antiviral Activity Against Effects of Herpes Simplex Virus Type 1 Infection

| Compound | Dose[a] (mg/kg/day) | Survivors/ Total (%) | Mean Survival Time (days) |
|---|---|---|---|
| Placebo[b] | — | 1/12 (0) | 12.5 ± 3.0 |
| Compound 7 | 200 | 6/12 (50)[c] | 11.0 ± 1.7 |
| Compound 7 | 100 | 4/12 (25) | 11.4 ± 1.8 |
| Compound 7 | 50 | 8/12 (75)[c] | 14.8 ± 5.0 |

[a]Treatments were once a day at −48, −24, and −2 hours relative to virus inoculation.
[b]A 2% sodium bicarbonate solution was used as the placebo and as diluent for Compound 7.
[c]Statistically significant (.025) difference between the drug-treated and placebo control mice, determined by the two-tailed Fisher exact test.

As is shown in Table 10 prophylactic treatment of a Herpes type 1 infection in mice was effectively treated with compound 7. There was some variability in the response with the response at 100 mg per kg dose being less effective than both the lower and higher dosages.

TABLE 11

Antiviral Activity Against
Herpes Simplex Virus Type 2 Infection

| Compound | Dose[a] (mg/kg/day) | Survivors/ Total (%) | Mean Survival Time (days) |
|---|---|---|---|
| Placebo[b] | — | 0/12 (8) | 9.8 ± 1.0 |
| Compound 7 | 200 | 2/12 (17) | 7.2 ± 3.9[c] |
| Compound 7 | 100 | 6/12 (50) | 11.2 ± 1.5[d] |
| Compound 7 | 50 | 6/12 (50) | 11.8 ± 2.3[d] |

[a]Treatments were once a day at −48, −24 and −2 hours relative to virus inoculation.
[b]A 2% sodium bicarbonate solution was used as the placebo and as diluent for Compound 7.
[c]Statistically significant ($p < .05$) difference between the drug-treated and placebo control mice, determined by the two-tailed t-test. Three mice died on days 1 and 2 post-virus inoculation from drug toxicity. The rest of the mice died at 9.6 ± 0.8 days which was about the same as the virus control.
[d]Statistically significant ($p < .05$) difference between the drug-treated and placebo control mice, determined by the two-tailed t-test.

As is shown in Table 11 prophylactic treatment of a Herpes type 2 infection was effective at all levels tested. At 50 and 100 mg per kg this statisticaly significance in mean survival time was just outside of the range of a statistical significance of $p < 0.1$ by the two-tailed Fisher exact test. At 200 mg per kg in the mouse the dose was partially toxic.

EXAMPLE 35

Antiviral Activity Against Influenza B Virus Infection in Mice

Compound 7 was tested therapeutically against Influenza B Virus Infection in Mice. In addition to a saline control Ribavirin, a known antiviral, was utilized for test purposes. The results of this test is shown in Table 12.

TABLE 12

Antiviral Activity Against
Influenza B Virus Infection in Mice

| Compound | Dose (mg/kg/day) | Treatment Schedule | Survivors/ Total (%) | Mean Survival Time (days) |
|---|---|---|---|---|
| Saline | — | a | 0/12 (0) | 8.7 ± 2.7 |
| Ribavirin | 100 | a | 10/12 (83)[c] | 8.0 ± 0.0 |
| Compound 7 | 100 | b | 2/12 (17) | 6.6 ± 1.1 |
|  | 50 | b | 2/12 (17) | 6.4 ± 1.5 |

[a]Half-daily doses were administered twice a day for 7 days starting 2 hours pre-virus inoculation.
[b]Treated once a day at −2 hours and on days 2, 4, and 6 relative to virus inoculation.
[c]$p < .001$ two-tailed t-test.

As is shown in Table 12 against influenza B in the mouse compound 7 as an efficacy between saline, having no antiviral activity against influenza, and Ribavirin, which has significant antiviral activity against influence.

EXAMPLE 36

Antiviral Activity Against San Angelo Virus Infection in Mice

In this example the antiviral activity against a San Angelo virus, an encephalitis type virus, was measured utilizing both a therapeutical and a prophylatic protocol. The results of this test are given i Table 13. As with the prior example Ribavirin was utilized as a positive antiviral control and saline as a negative. The results of this test is given in table 13.

TABLE 13

Antiviral Activity Against
San Angelo Virus Infection in Mice

| Compound | Dose (mg/kg/day) | Treatment Schedule | Survivors/ Total (%) | Mean Survival Time (21 days) |
|---|---|---|---|---|
| Saline | — | a | 2/12 (17) | 7.5 ± 1.2 |
| Ribavirin | 200 | a | 11/12 (92)[e] | 12.3 ± 2.9 |
| Compound 7 | 200 | b | 12/12 (100)[e] | >21 |
|  | 100 | c | 12/12 (100)[e] | >21 |
|  | 50 | c | 12/12 (100)[e] | >13.0 ± 0.0 |
| Compound 7 | 200 | d | 12/12 (100)[e] | >21 |

[a]Half-daily doses were administered twice a day for 7 days starting 2 hours pre-virus inoculation.
[b]Treated once a day at −2 hours and on days 2, 4, and 6 relative to virus inoculation. Half daily doses were administered twice a day.
[c]Treated once a day at −2 hours and on days 2, 4, and 6 relative to virus inoculation.
[d]Half-daily doses were administered at 24 and 16 hours pre-virus inoculation.
[e]$p < .02$ two-tailed Fisher exact.

As is evident from Table 13 in both a therapeutic and a prophylactic mode compound 7 showed antiviral activity equal to that of Ribavirin against San Angelo encephalitis virus.

EXAMPLE 37

Antiviral Activity Against Mouse Cytomegalovirus Infection in Mice

In this test compound 7 was also tested for both therapeutic or prophylactic efficacy against a mouse cytomegalovirus infection. The results of these tests are shown in Table 14 and 15.

TABLE 14

Antiviral Activity Against Mouse Cytomegalovirus Infection in Mice

| Compound | Dose (mg/kg/day) | Treatment Schedule | Survivors/ Total (%) | Mean Survival Time (days) |
|---|---|---|---|---|
| Saline | — | a | 4/12 (33) | 6.1 ± 0.4 |
| Compound 7 | 200 | a | 12/12 (100)[c] | >21 |
|  | 100 | b | 7/12 (58) | 7.0 ± 1.4 |
|  | 50 | b | 6/12 (50) | 6.5 ± 0.8 |

[a]Half-daily doses were administered at 24 and 16 hours pre-virus inoculation
[b]Single dose was administered 24 hours pre-virus inoculation
[c]$p < .005$ two-tailed Fisher exact test

TABLE 15

Antiviral Activity Against Mouse Cytomegalovirus Infection in Mice

| Compound | Dose (mg/kg/day) | Treatment Schedule | Survivors/ Total (%) | Mean Survival Time (days) |
|---|---|---|---|---|
| Saline | — | a | 3/12 (25) | 6.1 ± 0.9 |
| Compound 7 | 100 | b | 0/12 (0) | 6.0 ± 0.8 |

TABLE 15-continued

| Antiviral Activity Against Mouse Cytomegalovirus Infection in Mice | | | | |
|---|---|---|---|---|
| Compound | Dose (mg/kg/day) | Treatment Schedule | Survivors/ Total (%) | Mean Survival Time (days) |
| | 50 | b | 0/12 (0) | 6.3 ± 1.1 | a Treatments were once a day for 6 days starting 2 hours pre-virus inoculation
b Treatments were once a day at -2 hours and on days 2, 4, and 6 relative to virus inoculation As is evident at the 200 mg per kg dose compound 7 exhibited a 100% cure when tested in a prophylactic mode. However, as is seen in Table 15 this activity was not repeated in a therapeutic mode.

EXAMPLE 38

Antiviral Activity Against Semliki Forest Virus Infection in Mice

Antiviral activity was also tested against Semliki Forest Virus an Encephalitis type virus. In this example compound 7 was also tested for both therapeutic and prophylactic efficacy. Results of this test are shown in Table 16 for the therapeutic mode and in Table 17 for the prophylactic mode.

TABLE 16

| Antiviral Activity Against Semliki Forest Virus Infection in Mice | | | | |
|---|---|---|---|---|
| Compound | Dose (mg/kg/day) | Treatment Schedule | Survivors/ Total (%) | Mean Survival Time (days) |
| Saline | — | a | 0/12 (0) | 6.7 ± 1.9 |
| Compound 7 | 200 | b | 7/12 (58)$^e$ | 4.2 ± 0.8 |
| | 100 | c | 8/12 (67)$^e$ | 7.3 ± 0.5 |
| | 50 | c | 4/12 (33) | 6.6 ± 0.8 | a Half-daily doses were administered twice a day for 7 days starting 2 hours pre-virus inoculation
b Treated at -2 hours and on days 2, 4, and 6 relative to virus inoculation. Half-daily doses were administered twice a day because of insolubility
c Treated once a day at -2 hours and on days 2, 4, and 6 relative to virus inoculation
d Half-daily doses were administered at 24 and 16 hours pre-virus inoculation
$^e$ p < .01 two-tailed Fisher

TABLE 17

| Prophylactic Antiviral Activity Against Semliki Forest Virus Infection in Mice | | | | |
|---|---|---|---|---|
| Compound | Dose (mg/kg/day) | Treatment Schedule | Survivors/ Total (%) | Mean Survival Time (days) |
| Saline | — | d | 1/8 (12) | 10.4 ± 1.3 |
| Compound 7 | 200 | d | 4/8 (50) | 11.8 ± 2.9 | a Half-daily doses were administered twice a day for 7 days starting 2 hours pre-virus inoculation
b Treated at -2 hours and on days 2, 4, and 6 relative to virus inoculation. Half-daily doses were administered twice a day because of insolubility
c Treated once a day at -2 hours and on days 2, 4, and 6 relative to virus inoculation
d Half-daily doses were administered at 24 and 16 hours pre-virus inoculation
$^e$ p < .01 two-tailed Fisher As is evident from Tables 16 and 17 compound 7 exhibited antiviral activity in both a therapeutic mode and a prophylactic mode against this virus.

As is evident from the above tables antiviral activity against a variety of viruses is seen. In a further test little or no antiviral activity for compound 7 was demonstrated against influenza B virus and Friend Leukemia virus induced spleenmegleoma.

EXAMPLE 39

Antiviral Activity of Nucleosides and Nucleotides on Murine Natural Killer Cell Activity In Vitro Other compounds of the invention were tested with respect to their natural killer cell activity utilizing mouse spleen cells as per example 25 above. The results of these tests are tabulated in Table 18.

TABLE 18

| Effect of Guanosine Nucleosides and Nucleotides on Murine Natural Killer Cell Activity In Vitro$^a$ | | | |
|---|---|---|---|
| Exp # | Effector Cells Pretreated with: | Concentration (mM) | % Natural Killer Cell Cytotoxicity |
| 1 | None | — | 1.2 |
| | Compound 7 | 0.05 | 34.5 |
| | Compound 16 | 0.05 | 10 |
| | Compound 16 | 0.5 | 38 |
| | Compound 9 | 0.05 | 3 |
| | Compound 9 | 0.5 | 13 |
| 2 | None | — | 1.6 |
| | Compound 7 | 0.05 | 25 |
| | Compound 7 | 0.25 | 28 |
| | Compound 16 | 0.05 | 3 |
| | Compound 16 | 0.25 | 17 |
| | Compound 9 | 0.05 | 2 |
| 3 | None | — | 1.6 |
| | Compound 7 | 0.05 | 28 |
| | Compound 16 | 0.05 | 14 |
| | Compound 16 | 0.25 | 24 |
| | Compound 9 | 0.05 | 0.31 |
| | Compound 9 | 0.5 | 6.5 |

$^a$Spleen cells from mice were incubated in the absence and presence of various compounds. After incubation, cells were suspended in complete medium and then their cytotoxic activity was determined against YAC-1 target cells as described in the text

EXAMPLE 40

Effect of Nucleosides and Nucleotides on Human Natural Killer Cell Activity In Vitro Other Nucleosides and Nucleotides of the invention were tested for their activity in human natural killer cells in vivo as per example 26 above. The results are tabulated in Table 19.

TABLE 19

Effect of Guanosine Nucleosides and Nucleotides on Human Natural Killer Cell Activity In Vitro

| Exp # | Effector Cells Pretreated with: | Concentration (mM) | % Natural Killer Cell Cytotoxicity |
|---|---|---|---|
| 1 | None | — | 26 |
|  | Compound 7 | 0.4 | 91 |
|  | Compound 16 | 0.4 | 69 |
|  | Compound 12 | 0.4 | 39 |
|  | Compound 11 | 0.4 | 63 |
| 2 | None | — | 23 |
|  | Compound 12 | 0.2 | 43 |
| 3 | None | — | 17 |
|  | Compound 12 | 0.4 | 22 |
| 4 | None | — | 9 |
|  | Compound 11 | 0.4 | 19 |
| 5 | None | — | 3 |
|  | Compound 7 | 0.4 | 37 |
|  | Compound 16 | 0.4 | 10 |
|  | Compound 9 | 0.05 | 6 |
| 6 | None | — | 16.53 |
|  | Compound 7 | 0.4 | 50 |
|  | None | — | 40 |
|  | Compound 9 | 0.2 | 43 |
| 7 | None | — | 4.5 |
|  | Compound 7 | 0.2 | 10 |
|  | Compound 8 | 0.2 | 5 |
|  | Compound 19 | 0.2 | 7 |

EXAMPLE 41

Tumoricidal Activity of Macrophages In Mice

The activity of compound 7 with respect to its ability to activate macrophages was tested by injecting CBA/-CaJ mice with a single dose of compound 7 (2 mg per mouse) and after 24 hours the cytotoxcity of the spleen cells (SC), non adherent SC and adherent SC was determined. The results are shown in Table 20.

TABLE 20

Activation of Macrophages following Single Injection of Compound 7 in Mice[a]

| Effector Cells | Dose (mg) of Compound 7/mouse | % Cytotoxicity Assay 4 hrs. | 20 hrs. |
|---|---|---|---|
| Spleen Cells (SC) | None | 15 | 41 |
| Nonadherent (SC) | 2 | 45 | 70 |
| Adherent cells | 2 | 37 | 69 |

[a]A group of four mice (CBA/CaJ) were injected with 2 mg/mouse of compound 7 solution. Control group received saline. After 24 hours of injection, spleens were harvested. Adherent and nonadherent cells were separated by incubation of spleen cells on plastic plates for one hour. Cell suspension of spleen cells, nonadherent cells (NC) and adherent cells (AC) were prepared in complete medium. Cytotoxicity of SC, NC and AC was then measured against YAC-1 tumor target cells in 4 hrs and 20 hrs chromium release assay.

As is evident from Table 20 compound 7 was able to activate both natural killer and adherent (macrophage) cells as evidenced by the ability of these cells to exert augmented cytotoxicity against tumor target cells.

In examples 42 and 43 the combination activity of compounds of the invention with the known antiviral agent Ribavirin against San Angelo Virus and Banzi Virus were measured utilizing compound 7 in a prophylatic protocol. The RibavirIn served as a further antiviral agent for use in combination with the compounds of the invention.

EXAMPLE 42

Combination Chemotherapy Against San Angelo Virus In Mice

The combination chemotherapy results against San Angelo Virus in Mice are shown in Table 21.

TABLE 21

Combination Chemotherapy Against San Angelo Virus

| Treatment[a] | | Survivors/ Total (%) | Mean Survival Time[b] (Days) |
|---|---|---|---|
| −24 Hrs | Days 0–6 | | |
| Saline | Saline | 1/16 (6) | 8.3 ± 1.8[c] |
| Compound 7 (5)[d] | Saline | 7/16 (44)[e] | 9.6 ± 1.6 |
| Saline | Ribavirin (50) | 6/16 (38) | 9.0 ± 1.2 |
| Saline | Ribavirin (25) | 9/16 (56)[e] | 8.1 ± 0.7 |
| Compound 7 (5) | Ribavirin (50) | 8/16 (50)[e] | 8.9 ± 2.2 |
| Compound 7 (5) | Ribavirin (25) | 6/16 (38) | 10.1 ± 3.6 |

[a]A single injection of saline or compound 7 was given 24 hours before virus inoculation. Treatments on days 0–6 were twice a day for 7 days starting 2 hours pre-virus inoculation.
[b]Of mice that died.
[c]Standard Deviation.
[d]The dose in mg/kg/day is in parentheses.
[e]Statisically significant (p < .05), determined by the two-tailed Fisher exact test.

EXAMPLE 43

Combination Chemotherapy Against Banzi Virus Infection In Mice

The combination chemotherapy results against Banzi Virus infection in mice are shown in Table 22.

TABLE 22

Combination Chemotherapy Against Banzi Virus Infection

| Treatment[a] −24 hours | Treatment[b] days 0–6 | Survivors/ Total (%) | Mean Survival Time[c] (days) |
|---|---|---|---|
| Placebo[d] | Saline | 0/12 (0) | 7.7 ± 0.5 |
| Placebo | Ribavirin 100 mg/kg | 0/12 (0) | 8.5 ± 1.0[e] |
| Placebo | Ribavirin 200 mg/kg | 0/12 (0) | 9.1 ± 0.8[e] |
| Compound 7 100 mg/kg | Saline | 0/12 (0) | 9.3 ± 1.0[e] |
| Compound 7 100 mg/kg | Ribavirin 100 mg/kg | 0/12 (0) | 10.2 ± 0.9[e] |
| Compound 7 | Ribavirin | 3/12 (25) | 12.4 ± 3.5[e] |

[a]Single injection given 24 hours before virus inoculation.
[b]Half-daily doses given twice a day for 7 days starting 2 hours pre-virus inoculation.
[c]Of mice that died. Survivors lived 21 days.
[d]A 2% sodium bicarbonate solution was the placebo and diluent for compound 7. Ribavirin was dissolved in saline.
[e]Statistically significant (p < .05), determined by a two-tailed t-test.

As is evident from Tables 21 and 22, compound 7 in a prophylactic mode in combination with the known antiviral Ribavirin, exhibited efficacy against the test viruses.

The compounds of the invention can be given to a warm blooded host in need thereof in appropriate formulations wherein the compounds comprise the active ingredient of the formulations. Thus the compounds of the invention can be made up into injectables suitable for intravenous or other type injection into the host animal. Further they can be given in an appropriate oral formulation as for instance as an oral syrup preparation, an oral capsule or oral tablet. An additional route of administration might be as a suppository.

For an injectable the compounds would be dissolved in a suitable solution as for instance in a sodium bicarbonate or other buffer. Such a solution would be filtered and added to appropriate ampules or vials and sealed and sterilized.

As a syrup, the compounds in buffered solution would be mixed with an appropriate syrup with mild stirring. For capsules the dry compounds would be blended with appropriate fillers, binders or the like as for instance Lactose USP powder or Sterotex powder. For the preparation of tablets the compounds of the invention would be mixed with suitable binders and fillers as for instance corn starch NF, Microcrystalline Cellulose, Sterotex powder and water and dried to a low water content. This would be followed by screening, milling, further screening and pressing into the appropriate tablets.

For suppositories, the compounds would be dissolved into appropriate melts of Polyethylene Glycol as for instance Polyethylene Glycol 1540 and 8000 at 60° and formed into the suppositories by molding at 25°.

In addition to the above formulations, the compounds of the invention could also be administered utilizing other delivery technic such as incorporating the compounds of the invention with liposomes and the like.

Additionally, prodrug forms of the compounds of the invention could be utilized to facilitate dispensing, uptake, absorption, metabolic control and the like. One such prodrug would be the tri-acetate ester of compound 7. Further prodrugs might allow for enzymatic conversion in vivo of analogs of the compounds of the invention into compounds of the invention.

For the purpose of brevity in certain chemical figures and schemes of this specification and the claims attached hereto, different tautomeric forms of the heterocycles of certain compounds have been shown between the vaarious figures and schemes. It is understood that regardless of whether or not substituents are shown in their enol or their keto form, they represent the same compound. Thus, in the claims, the abstract and the brief description in order to utilize only a single structural figure, oxygen and sulfur substituents in the 5 and 7 ring positions are shown in an enolate form whereas in the various schemes these substituents are shown in their normal keto form.

What is claimed is:

1. A method of treating viral diseases in mammals which consists of
administering to said mammals a therapeutic effective amount of a compound of the structure:

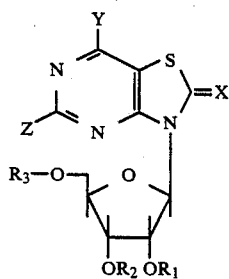

wherein $R_1$ and $R_2$ individually are H or $C_1$–$C_{18}$ acyl and $R_3$ is H, $C_1$–$C_{18}$ acyl or

or $R_1$ is H and together $R_2$ and $R_3$ are

and X is =O or =S, Y is —OH, —SH, and Z is H, —NH$_2$, or a pharmaceutically acceptable salt thereof.

2. A method of claim 1 wherein:
Z is —NH$_2$, Y is —OH and X is =O or =S.

3. A method of claim 2 wherein:
$R_1$ and $R_2$ are H, acetyl or benzoyl and $R_3$ is H, acetyl, benzoyl or

or $R_1$ is H and together $R_2$ and $R_3$ are

or a pharmaceutically acceptable salt thereof.

4. A method of claim 3 wherein:
X is =O.

5. A method of claim 4 wherein:
$R_1$ and $R_2$ are H.

6. A method of claim 5 wherein:
$R_3$ is H.

7. A pharmaceutical composition containing a therapeutically effective amount of 5-amino-3-β-D-ribofuranosylthiazolo[4,5-d]pyrimidin-2,7(6H)-dione or a pharmaceutically acceptable salt thereof in combination with a therapeutically acceptable diluent or carrier.

8. A pharmaceutical composition containing a prophylactically effective amount of 5-amino-3-β-D-ribofuranosylthiazolo[4,5-d]pyrimidin-2,7(6H)-dione or a pharmaceutically acceptable salt thereof in combination with an acceptable diluent or carrier.

9. A method of treating rhabdovirus, picornavirus, coronavirus, togavirus, bunyavirus, flavivirus, herpesvirus and cytomegalovirus in an afflicted host, said method consisting of:
administering to said host a therapeutic effective amount of the compound 5-amino-3-β-D-ribofuranosylthiazolo[4,5-d]pyrimidin-2,7(6H)-dione.

10. A method of treating rhabdovirus, picornavirus, coronavirus, togavirus, bunyavirus, flavivirus, herpesvirus and cytomegalovirus in an afflicted host, said method consisting of:
administering to said host a therapeutic effective amount of a compound of the structure:

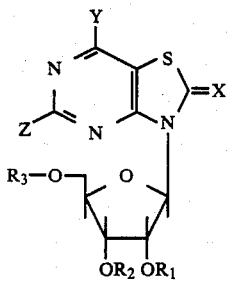

wherein $R_1$ and $R_2$ individually are H or $C_1$–$C_{18}$ acyl and $R_3$ is H, $C_1$–$C_{18}$ acyl or

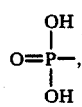

or $R_1$ is H and together $R_2$ and $R_3$ are

and X is =O or =S, Y is —OH, —SH, and Z is H, —NH$_2$, or a pharmaceutically acceptable salt thereof.

11. A method of claim 10 wherein:
Z is —NH$_2$, Y is —OH and X is =O or =S.

12. A method of claim 11 wherein:
$R_1$ and $R_2$ are H, acetyl or benzoyl and $R_3$ is H, acetyl, benzoyl or

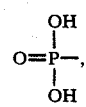

or $R_1$ is H and together $R_2$ and $R_3$ are

or a pharmaceutically acceptable salt thereof.

13. A method of claim 12 wherein:
X is =O.

14. A method of claim 13 wherein:
$R_1$ and $R_2$ are H.

15. A method claim 14 wherein:
$R_3$ is H.

16. A method of treating togavirus, bunyavirus, flavivirus, herpesvirus and cytomegalovirus in an afflicted host, said method consisting of:
administering to said host a therapeutic effective amount of the compound 5-amino-3-β-D-ribofuranosylthiazolo[4,5-d]pyrimidin-2,7(6H)-dione.

17. A method of treating togavirus, bunyavirus, flavivirus, herpesvirus and cytomegalovirus in an afflicted host, said method consisting of:
administering to said host a therapeutic effective amount of a compound of the structure:

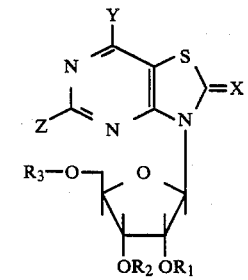

wherein $R_1$ and $R_2$ individually are H or $C_1$–$C_{18}$ acyl and $R_3$ is H, $C_1$–$C_{18}$ acyl or

or $R_1$ is H and together $R_2$ and $R_3$ are

and X is =O or =S, Y is —OH, —SH, and Z is H, —NH$_2$ or a pharmaceutically acceptable salt thereof.

* * * * *